(12) United States Patent
Inagaki et al.

(10) Patent No.: US 9,084,831 B2
(45) Date of Patent: *Jul. 21, 2015

(54) MOLECULAR PROBE PRECURSOR FOR IMAGING OF PANCREATIC ISLET, AND USE THEREOF

(75) Inventors: Nobuya Inagaki, Kyoto (JP); Hideo Saji, Kyoto (JP); Kentaro Toyoda, Kyoto (JP); Hiroyuki Kimura, Kyoto (JP); Konomu Hirao, Kyoto (JP); Kenji Nagakawa, Kyoto (JP)

(73) Assignees: Kyoto University, Kyoto (JP); ARKRAY, Inc., Kyoto (JP)

( * ) Notice: Subject to any disclaimer, the term of this patent is extended or adjusted under 35 U.S.C. 154(b) by 664 days.

This patent is subject to a terminal disclaimer.

(21) Appl. No.: 13/050,672

(22) Filed: Mar. 17, 2011

(65) Prior Publication Data

US 2011/0171129 A1 Jul. 14, 2011

Related U.S. Application Data

(63) Continuation-in-part of application No. PCT/JP2009/056628, filed on Mar. 31, 2009.

(30) Foreign Application Priority Data

| Sep. 20, 2008 | (JP) | ................................ | 2008-241889 |
| Jan. 9, 2009 | (JP) | ................................ | 2009-003042 |
| Mar. 17, 2009 | (JP) | ................................ | 2009-064849 |
| Mar. 23, 2009 | (JP) | ................................ | 2009-070517 |

(51) Int. Cl.
*A61K 51/08* (2006.01)

(52) U.S. Cl.
CPC ............... *A61K 51/088* (2013.01); *A61K 51/08* (2013.01)

(58) Field of Classification Search
None
See application file for complete search history.

(56) References Cited

U.S. PATENT DOCUMENTS 6,821,949 B2 * 11/2004 Bridon et al. .................. 514/5.9
2009/0180953 A1   7/2009 Gotthardt et al.

FOREIGN PATENT DOCUMENTS

| EP | 1867634 | 12/2007 |
| JP | 09-292466 | 11/1997 |
| WO | WO 2004/035744 | 4/2004 |
| WO | WO 2006/107106 | 10/2006 |

OTHER PUBLICATIONS

Gotthardt et al., Regulatory peptides, 2006, 137, 162-167.*
Runge et al., Biochemistry, 2007, 46(19) 5830-5840.*
Goke et al., J. Bio. Chem., 1993, 268(26) 19650-19655.*

Arkray, Inc., "Leading research on molecular imaging device for supporting treatment of malignant tumor, etc. / Development of method for ultra-early diagnosis of diabetes by noninvasive in-vivo pancreatic islets imaging", Interim annual report of Heisei 19 (2007) fiscal year, out of Heisei 19 to 20 (2007-2008) Fiscal years (Sep. 19, 2008) (Partial (1, 5) translation provided).

S. Al-Sabah et al., "The positive charge at Lys-288 of the glucagon-like peptide-1 (GLP-1) receptor is important for binding the N-terminus of peptide agonists", FEBS Letters 553: 342-346 (2003).

M. Behe et al., "Are radiolabeled GLP-1 receptor antagonists useful for scintigraphy?", 2009 SNM Annual Meeting, abstract, Oral Presentations No. 327 (2009).

M. Brom et al., "$^{68}$Ga-labelled exendin-3, a new agent for the detection of insulinemas with PET", Eur. J. Nucl. Med, Mol. Imaging 37: 1345-1355 (2010).

E. Christ et al., "Glucagon-Like Peptide-1 Receptor Imaging for Localization of Insulinomas", J. Clin. Endocrinol Metab. 94(11): 4398-4405 (2009).

R. Goke et al "Exendin-4 is a High Potency Agonist and Truncated Exendin-(9-39)-amide an Antagonist at the Glucagon-like Peptide 1-(7-36)-amide Receptor of Insulin-secreting β-Cells", J. Biol. Chem. 268(26): 19650-19655 (1993).

(Continued)

*Primary Examiner* — Karlheinz R Skowronek
*Assistant Examiner* — Roy Teller
(74) *Attorney, Agent, or Firm* — Morgan, Lewis & Bockius LLP

(57) ABSTRACT

A precursor of a molecular probe for imaging of pancreatic islets is provided. The precursor includes a polypeptide represented by any one of the following formulae (1) to (12), or a polypeptide having a homology with the foregoing polypeptide:

```
*-DLSKQMEEEAVRLFIEWLK*NGGPSSGAPPPS-NH₂   (1)
*-LSKQMEEEAVRLFIEWLK*NGGPSSGAPPPS-NH₂    (2)
*-SKQMEEEAVRLFIEWLK*NGGPSSGAPPPS-NH₂     (3)
*-KQMEEEAVRLFIEWLK*NGGPSSGAPPPS-NH₂      (4)
*-DLSK*QMEEEAVRLFIEWLKNGGPSSGAPPPS-NH₂   (5)
*-LSK*QMEEEAVRLFIEWLKNGGPSSGAPPPS-NH₂    (6)
*-SK*QMEEEAVRLFIEWLKNGGPSSGAPPPS-NH₂     (7)
*-K*QMEEEAVRLFIEWLKNGGPSSGAPPPS-NH₂      (8)
DLSK*QMEEEAVRLFIEWLK*NGGPSSGAPPPS-NH₂    (9)
LSK*QMEEEAVRLFIEWLK*NGGPSSGAPPPS-NH₂    (10)
SK*QMEEEAVRLFIEWLK*NGGPSSGAPPPS-NH₂     (11)
K*QMEEEAVRLFIEWLK*NGGPSSGAPPPS-NH₂      (12)
```

19 Claims, 8 Drawing Sheets

(56) References Cited

OTHER PUBLICATIONS

M. Gotthardt et al., "Use of the incretin hormone glucagon-like peptide-1 (GLP-1) for the detection of insulinomas: initial experimental results", European Journal of Nuclear Medicine 29(5): 598-606 (2002).

M. Gotthardt et al.,"A new technique for in vivo imaging of specific GLP-1 binding sites: First results in small rodents". Regulatory Peptides 137: 162-167 (2006).

B.D. Green et al., "Chronic treatment with exendin(9-39)amide indicates a minor role for endogenous glucagon-like peptide-1 in metabolic abnormalities of obesity-related diabetes in ob/ob mice", J. Endocrinol. 185: 307-317 (2005).

K. Hirao, "Leading research on molecular imaging device for supporting treatment malignant tumor, etc. / Development of method for ultra-early diagnosis of diabetes by noninvasive in-vivo pancreatic islet imaging", Interim report of Heisei 20 (2008) Fiscal Year, out of Heisei 19 to 20 (2007-2008) years (May 20, 2009) (Partial pp. 1, 2) translation provided).

N. Inagaki, "Research on development of method for ultra-early diagnosis of diabetes by noninvasive in-vivo pancreatic islet imaging", Heisei 19 (2007) Fiscal Year Overview Research Report, Research Project for Medical Equipment Development Promotion, Grants-in-Aid for Scientific Research from Ministry of Health, Labor and Welfare (Apr. 20, 2008) (Partial (pp. 1-7, 10-15, 24, 25) translation provided).

N. Inagake "Research on development of method for ultra-early diagnosis of diabetes by noninvasive in-vivo pancreatic islet imaging", Heisei 20 (2008) Fiscal Year Overview Research Report. Research Project for Medical Equipment Development Promotion, Grants-in-Aid for Scientific Research from Ministry of Health, Labor and Welfare (Apr. 21, 2009) (Partial (pp. 1-7, 10-17, 23, 24) translation provided).

N. Inagaki, "Development of method for ultra-early diagnosis of diabetes by noninvasive in-vivo pancreatic islet imaging", Research of New Medical Devices 13, 72-73 (Mar. 25, 2008) (Partial (pp. 72, 73) translation provided).

H. Kimura et al., "Development of in vivo imaging agents targeting glucagon-like peptide-1 receptor (GLP-1R) in pancreatic islets", 2009 SNM Annual Meeting, Abstract, Oral Presentations No. 326 (2009).

E. Mukai et al., "Non-invasive imaging of pancreatic islets targeting glucagon-like peptide-1-receptors", 44th EASD Annual Meeting (Rome), abstract, Presentation No. 359 (2008).

E. Mukai et al., "GLP-1 receptor antagonist as a potential probe for pancreatic B-cell imaging", Biophys. Res. Commun. 389(3): 523-526 (2009).

J. W. Neidigh et al., "Exendin-4 and Glucagon-like peptide-1: NMR Structural Comparisons in the Solution and Micelle-Associated State", Biochemistry 40. 13188-13200 (9001).

U. Ritzel et al. "A synthetic glucagon-like peptide-1 analog with improved plasma stability", Journal of Endocrinology 159: 93-102 (1998).

J. Schirra et al., "Exendin(9-39)amide Is an Antagonist of Glucagon-like Peptide-1)7-36)amide in Humans", J. Clin. Invest. 101(7): 1421-1430 (1998).

G. Vaidyanathan et al., "Protein Radiohalogenation: Observations on the Design of N-Succinimidyl Ester Acylation Agents", Bioconjug. Chem. 1(4), 269-273 (1990).

G. Vaidyanathan et al., "Radioiodination of Proteins Using N-Succinimidyl 4-Hydroxy-3-iodobenzoate", Bioconjug. Chem. 4(1), 78-84 (1993).

A. Wicki et al., "[Lys$^{40}$(Ahx-DTPA-$^{111}$In)NH$_2$]-Exendin-4 Is a Highly Efficient Radiotherapeutic for Glucagon-Like Peptide-1 Receptor-Targeted Therapy for Insulinoma", Clin. Cancer Res. 13(12): 3696-3705 (2007).

D. Wild et al., "[Lys$^{40}$(Ahx-DTPA-$^{111}$In)NH$_2$]Exendin-4, a Very Promising Ligand for Glucagon-like Peptide-1 (GLP-1) Receptor Targeting", J. Nucl. Med. 47: 2025-2033 (2006).

International Search Report issued in PCT application No PCT/JP2009/056628 (May 19, 2009).

Mukai et al., "Non-Invasive Imaging of Pancreatic Islets Targeting Glucagon-Like Peptide-1 Receptors," Diabetes, 58: A371 (2009).

Extended European Search Report issued in counterpart European Patent Application No. 09814677.2 dated Apr. 1, 2014.

Kung et al., "In Vivo Imaging of β-Cell Mass in Rats using 81F-FP-(+)-DTBZ: A Potential PET Ligand for Studying Diabetes Mellitus," The Journal of Nuclear Medicine, 49: 1171-1176 (2008).

Office Action issued in Japanese Patent Application No. 2010-242128 dated Aug. 20, 2013.

* cited by examiner

```
                       SEQUENCE LISTING

<160> NUMBER OF SEQ ID NOS: 12

<210> SEQ ID NO 1
<211> LENGTH: 31
<212> TYPE: PRT
<213> ORGANISM: Artificial Sequence
<220> FEATURE:
<223> OTHER INFORMATION: A precursor of imaging probe for pancreas islet
<220> FEATURE:
<221> NAME/KEY: MOD_RES
<222> LOCATION: (1)..(1)
<223> OTHER INFORMATION: Amino group of N-terminus is protected by a
      protecting group.
<220> FEATURE:
<221> NAME/KEY: MOD_RES
<222> LOCATION: (19)..(19)
<223> OTHER INFORMATION: Amino group of side chain is protected by a
      protecting group.
<220> FEATURE:
<221> NAME/KEY: MOD_RES
<222> LOCATION: (31)..(31)
<223> OTHER INFORMATION: Carboxyl group of C-terminus is amidated.

<400> SEQUENCE: 1

Asp Leu Ser Lys Gln Met Glu Glu Glu Ala Val Arg Leu Phe Ile Glu
1               5                   10                  15

Trp Leu Lys Asn Gly Gly Pro Ser Ser Gly Ala Pro Pro Pro Ser
            20                  25                  30

<210> SEQ ID NO 2
<211> LENGTH: 30
<212> TYPE: PRT
<213> ORGANISM: Artificial Sequence
<220> FEATURE:
<223> OTHER INFORMATION: A precursor of probe for pancreas islet imaging.
<220> FEATURE:
<221> NAME/KEY: MOD_RES
<222> LOCATION: (1)..(1)
<223> OTHER INFORMATION: Amino group of N-terminus is protected by a
      protecting group.
<220> FEATURE:
<221> NAME/KEY: MOD_RES
<222> LOCATION: (18)..(18)
<223> OTHER INFORMATION: Amino group of side chain is protected by a
      protecting group.
<220> FEATURE:
<221> NAME/KEY: MOD_RES
<222> LOCATION: (30)..(30)
<223> OTHER INFORMATION: Carboxyl group of C-terminus is amidated.

<400> SEQUENCE: 2

Leu Ser Lys Gln Met Glu Glu Glu Ala Val Arg Leu Phe Ile Glu Trp
1               5                   10                  15

Leu Lys Asn Gly Gly Pro Ser Ser Gly Ala Pro Pro Pro Ser
            20                  25                  30

<210> SEQ ID NO 3
<211> LENGTH: 29
<212> TYPE: PRT
<213> ORGANISM: Artificial Sequence
```

```
<220> FEATURE:
<223> OTHER INFORMATION: A precursor of probe for pancreas islet imaging.
<220> FEATURE:
<221> NAME/KEY: MOD_RES
<222> LOCATION: (1)..(1)
<223> OTHER INFORMATION: Amino group of N-terminus is protected by a
      protecting group.
<220> FEATURE:
<221> NAME/KEY: MOD_RES
<222> LOCATION: (17)..(17)
<223> OTHER INFORMATION: Amino group of side chain is protected by a
      protecting group.
<220> FEATURE:
<221> NAME/KEY: MOD_RES
<222> LOCATION: (29)..(29)
<223> OTHER INFORMATION: Carboxyl group of C-terminus is amidated.

<400> SEQUENCE: 3

Ser Lys Gln Met Glu Glu Glu Ala Val Arg Leu Phe Ile Glu Trp Leu
1               5                   10                  15

Lys Asn Gly Gly Pro Ser Ser Gly Ala Pro Pro Pro Ser
            20                  25

<210> SEQ ID NO 4
<211> LENGTH: 28
<212> TYPE: PRT
<213> ORGANISM: Artificial Sequence
<220> FEATURE:
<223> OTHER INFORMATION: A precursor of probe for pancreas islet imaging.
<220> FEATURE:
<221> NAME/KEY: MOD_RES
<222> LOCATION: (1)..(1)
<223> OTHER INFORMATION: Amino group of N-terminus is protected by a
      protecting group.
<220> FEATURE:
<221> NAME/KEY: MOD_RES
<222> LOCATION: (16)..(16)
<223> OTHER INFORMATION: Amino group of side chain is protected by a
      protecting group.
<220> FEATURE:
<221> NAME/KEY: MOD_RES
<222> LOCATION: (28)..(28)
<223> OTHER INFORMATION: Carboxyl group of C-terminus is amidated.

<400> SEQUENCE: 4

Lys Gln Met Glu Glu Glu Ala Val Arg Leu Phe Ile Glu Trp Leu Lys
1               5                   10                  15

Asn Gly Gly Pro Ser Ser Gly Ala Pro Pro Pro Ser
            20                  25

<210> SEQ ID NO 5
<211> LENGTH: 31
<212> TYPE: PRT
<213> ORGANISM: Artificial Sequence
<220> FEATURE:
<223> OTHER INFORMATION: A precursor of imaging probe for pancreas islet
<220> FEATURE:
<221> NAME/KEY: MOD_RES
<222> LOCATION: (1)..(1)
<223> OTHER INFORMATION: Amino group of N-terminus is protected by a
      protecting group.
<220> FEATURE:
<221> NAME/KEY: MOD_RES
<222> LOCATION: (4)..(4)
<223> OTHER INFORMATION: Amino group of side chain is protected by a
      protecting group.
<220> FEATURE:
<221> NAME/KEY: MOD_RES
<222> LOCATION: (31)..(31)
<223> OTHER INFORMATION: Carboxyl group of C-terminus is amidated.
```

```
<400> SEQUENCE: 5

Asp Leu Ser Lys Gln Met Glu Glu Ala Val Arg Leu Phe Ile Glu
1               5                   10                  15

Trp Leu Lys Asn Gly Gly Pro Ser Ser Gly Ala Pro Pro Pro Ser
            20                  25                  30

<210> SEQ ID NO 6
<211> LENGTH: 30
<212> TYPE: PRT
<213> ORGANISM: Artificial Sequence
<220> FEATURE:
<223> OTHER INFORMATION: A precursor of imaging probe for pancreas islet
<220> FEATURE:
<221> NAME/KEY: MOD_RES
<222> LOCATION: (1)..(1)
<223> OTHER INFORMATION: Amino group of N-terminus is protected by a
      protecting group.
<220> FEATURE:
<221> NAME/KEY: MOD_RES
<222> LOCATION: (3)..(3)
<223> OTHER INFORMATION: Amino group of side chain is protected by a
      protecting group.
<220> FEATURE:
<221> NAME/KEY: MOD_RES
<222> LOCATION: (30)..(30)
<223> OTHER INFORMATION: Carboxyl group of C-terminus is amidated.

<400> SEQUENCE: 6

Leu Ser Lys Gln Met Glu Glu Ala Val Arg Leu Phe Ile Glu Trp
1               5                   10                  15

Leu Lys Asn Gly Gly Pro Ser Ser Gly Ala Pro Pro Pro Ser
            20                  25                  30

<210> SEQ ID NO 7
<211> LENGTH: 29
<212> TYPE: PRT
<213> ORGANISM: Artificial Sequence
<220> FEATURE:
<223> OTHER INFORMATION: A precursor of imaging probe for pancreas islet
<220> FEATURE:
<221> NAME/KEY: MOD_RES
<222> LOCATION: (1)..(1)
<223> OTHER INFORMATION: Amino group of N-terminus is protected by a
      protecting group.
<220> FEATURE:
<221> NAME/KEY: MOD_RES
<222> LOCATION: (2)..(2)
<223> OTHER INFORMATION: Amino group of side chain is protected by a
      protecting group.
<220> FEATURE:
<221> NAME/KEY: MOD_RES
<222> LOCATION: (29)..(29)
<223> OTHER INFORMATION: Carboxyl group of C-terminus is amidated.

<400> SEQUENCE: 7

Ser Lys Gln Met Glu Glu Glu Ala Val Arg Leu Phe Ile Glu Trp Leu
1               5                   10                  15

Lys Asn Gly Gly Pro Ser Ser Gly Ala Pro Pro Pro Ser
            20                  25

<210> SEQ ID NO 8
<211> LENGTH: 28
<212> TYPE: PRT
<213> ORGANISM: Artificial Sequence
<220> FEATURE:
<223> OTHER INFORMATION: A precursor of imaging probe for pancreas islet
```

```
<220> FEATURE:
<221> NAME/KEY: MOD_RES
<222> LOCATION: (1)..(1)
<223> OTHER INFORMATION: Amino group of N-terminus and Amino group of
      side chain are protected by a protecting group.
<220> FEATURE:
<221> NAME/KEY: MOD_RES
<222> LOCATION: (28)..(28)
<223> OTHER INFORMATION: Carboxyl group of C-terminus is amidated.

<400> SEQUENCE: 8

Lys Gln Met Glu Glu Glu Ala Val Arg Leu Phe Ile Glu Trp Leu Lys
1               5                   10                  15

Asn Gly Gly Pro Ser Ser Gly Ala Pro Pro Pro Ser
            20                  25

<210> SEQ ID NO 9
<211> LENGTH: 31
<212> TYPE: PRT
<213> ORGANISM: Artificial Sequence
<220> FEATURE:
<223> OTHER INFORMATION: A precursor of imaging probe for pancreas islet
<220> FEATURE:
<221> NAME/KEY: MOD_RES
<222> LOCATION: (4)..(4)
<223> OTHER INFORMATION: Amino group of side chain is protected by a
      protecting group.
<220> FEATURE:
<221> NAME/KEY: MOD_RES
<222> LOCATION: (19)..(19)
<223> OTHER INFORMATION: Amino group of side chain is protected by a
      protecting group.
<220> FEATURE:
<221> NAME/KEY: MOD_RES
<222> LOCATION: (31)..(31)
<223> OTHER INFORMATION: Carboxyl group of C-terminus is amidated.

<400> SEQUENCE: 9

Asp Leu Ser Lys Gln Met Glu Glu Glu Ala Val Arg Leu Phe Ile Glu
1               5                   10                  15

Trp Leu Lys Asn Gly Gly Pro Ser Ser Gly Ala Pro Pro Pro Ser
            20                  25                  30

<210> SEQ ID NO 10
<211> LENGTH: 30
<212> TYPE: PRT
<213> ORGANISM: Artificial Sequence
<220> FEATURE:
<223> OTHER INFORMATION: A precursor of probe for pancreas islet imaging.
<220> FEATURE:
<221> NAME/KEY: MOD_RES
<222> LOCATION: (3)..(3)
<223> OTHER INFORMATION: Amino group of side chain is protected by a
      protecting group.
<220> FEATURE:
<221> NAME/KEY: MOD_RES
<222> LOCATION: (18)..(18)
<223> OTHER INFORMATION: Amino group of side chain is protected by a
      protecting group.
<220> FEATURE:
<221> NAME/KEY: MOD_RES
<222> LOCATION: (30)..(30)
<223> OTHER INFORMATION: Carboxyl group of C-terminus is amidated.

<400> SEQUENCE: 10

Leu Ser Lys Gln Met Glu Glu Glu Ala Val Arg Leu Phe Ile Glu Trp
1               5                   10                  15

Leu Lys Asn Gly Gly Pro Ser Ser Gly Ala Pro Pro Pro Ser
            20                  25                  30
```

```
<210> SEQ ID NO 11
<211> LENGTH: 29
<212> TYPE: PRT
<213> ORGANISM: Artificial Sequence
<220> FEATURE:
<223> OTHER INFORMATION: A precursor of probe for pancreas islet imaging.
<220> FEATURE:
<221> NAME/KEY: MOD_RES
<222> LOCATION: (2)..(2)
<223> OTHER INFORMATION: Amino group of side chain is protected by a
      protecting group.
<220> FEATURE:
<221> NAME/KEY: MOD_RES
<222> LOCATION: (17)..(17)
<223> OTHER INFORMATION: Amino group of side chain is protected by a
      protecting group.
<220> FEATURE:
<221> NAME/KEY: MOD_RES
<222> LOCATION: (29)..(29)
<223> OTHER INFORMATION: Carboxyl group of C-terminus is amidated.

<400> SEQUENCE: 11

Ser Lys Gln Met Glu Glu Glu Ala Val Arg Leu Phe Ile Glu Trp Leu
1               5                   10                  15

Lys Asn Gly Gly Pro Ser Ser Gly Ala Pro Pro Pro Ser
            20                  25

<210> SEQ ID NO 12
<211> LENGTH: 28
<212> TYPE: PRT
<213> ORGANISM: Artificial Sequence
<220> FEATURE:
<223> OTHER INFORMATION: A precursor of probe for pancreas islet imaging.
<220> FEATURE:
<221> NAME/KEY: MOD_RES
<222> LOCATION: (1)..(1)
<223> OTHER INFORMATION: Amino group of side chain is protected by a
      protecting group.
<220> FEATURE:
<221> NAME/KEY: MOD_RES
<222> LOCATION: (16)..(16)
<223> OTHER INFORMATION: Amino group of side chain is protected by a
      protecting group.
<220> FEATURE:
<221> NAME/KEY: MOD_RES
<222> LOCATION: (28)..(28)
<223> OTHER INFORMATION: Carboxyl group of C-terminus is amidated.

<400> SEQUENCE: 12

Lys Gln Met Glu Glu Glu Ala Val Arg Leu Phe Ile Glu Trp Leu Lys
1               5                   10                  15

Asn Gly Gly Pro Ser Ser Gly Ala Pro Pro Pro Ser
            20                  25
```

MOLECULAR PROBE PRECURSOR FOR IMAGING OF PANCREATIC ISLET, AND USE THEREOF

This application is a continuation-in-part of PCT/JP209/056628, filed Mar. 31, 2009 which claims priority to Japanese Application No. 2008-241889, filed Sep. 20, 2008; Japanese Application No. 2009-003042, filed Jan. 9, 2009; Japanese Application No. 2009-064849, filed Mar. 17, 2009 and Japanese Application No. 2009-070517, filed Mar. 23, 2009; all of which are hereby incorporated by reference in their entirety.

SEQUENCE LISTING SUBMISSION VIA EFS-WEB

A computer readable text file, entitled "068002-5031-SequencenceListing.txt," created on or about Mar. 17, 2011 with a file size of about 9 kb contains the sequence listing for this application and is hereby incorporated by reference in its entirety.

TECHNICAL FIELD

The present invention relates to a precursor of a molecular probe (hereinafter referred to as a molecular probe precursor) for imaging of pancreatic islets, and the use of the same.

BACKGROUND ART

Today, type-II diabetics are continuously increasing in Japan, and the estimated number of the same exceeds 8,200,000. As a measure against this increase, interventions for preventing diabetes from developing have been made based on the glucose tolerance test, resulting, however, in unsatisfactory effects. The cause is as follows: at such a borderline stage that functional abnormalities are found by the glucose tolerance test, disorders of pancreatic islets have already advanced to a high degree, and this stage possibly is too late as a time for starting interventions.

More specifically, in the diabetes developing process, the amount of pancreatic islets (particularly, the amount of pancreatic β-cells) decreases prior to the occurrence of glucose tolerance abnormalities. Therefore, when functional abnormalities are detected or there are subjective symptoms, diabetes has already reached the stage where it is too difficult to be treated. On the other hand, if a decrease in the amount of pancreatic islets and/or the amount of pancreatic β-cells can be detected at an early stage, there is a possibility for the prevention and treatment of diabetes. Therefore, a noninvasive technique for imaging of pancreatic islets, particularly a noninvasive technique for imaging of pancreatic islets for determining the amount of the pancreatic islets and/or the amount of pancreatic β-cells, has been desired for the prevention and diagnosis of diabetes. Among these, a molecular probe that enables the imaging of pancreatic islets, preferably the pancreatic β-cell imaging, has been desired in particular.

As a molecular probe for imaging pancreatic islets in a sliced section, exendin(9-39) is known, which is one of ligands of GLP-1R (glucagon-like peptide-1 receptor). More specifically, it is known that $^{125}$I labeled exendin(9-39) is administered to mice by intravenous injection through the tail vein, $^{125}$I labeled exendin(9-39) accumulates selectively and specifically in the pancreas among organs, and binds selectively to pancreatic islets in the pancreas (E. Mukai et al. Non-invasive imaging of pancreatic islets targeting glucagon-like peptide-1 receptors, 44thEASD Annual Meeting Rome 2008, abstract, Presentation No. 359 [on line] (Document 1)).

DISCLOSURE OF INVENTION

Problem to be Solved by the Invention

With the above-described $^{125}$I-labeled exendin(9-39), however, it has been difficult to perform noninvasive three-dimensional imaging. The present invention provides a molecular probe for imaging of pancreatic islets that enables noninvasive three-dimensional imaging of the pancreatic islets.

Means for Solving Problem

The present invention is a precursor of a molecular probe for use in imaging of pancreatic islets, the consisting of any one of the following polypeptides:

a polypeptide represented by any one of the following formulae (1) to (12);

a polypeptide obtained by deletion, insertion, or substitution of one to several amino acids with respect to a polypeptide represented by any one of the following formulae (1) to (12), the polypeptide being capable of binding to pancreatic islets after being labeled and deprotected; and a polypeptide having a homology of 80% or higher with any one of the amino acid sequences of polypeptides represented by the following formulae (1) to (12), the polypeptide being capable of binding to pancreatic islets after being labeled and deprotected, wherein the molecular probe is used in imaging of pancreatic islets,

```
                                              (SEQ ID NO. 1)
*-DLSKQMEEEAVRLFIEWLK*NGGPSSGAPPPS-NH2           (1)

(SEQ ID NO. 2)
*-LSKQMEEEAVRLEIEWLK*NGGPSSGAPPPS-NH2            (2)

(SEQ ID NO. 3)
*-SKQMEEEAVRLFIEWLK*NGGPSSGAPPPS-NH2             (3)

(SEQ ID NO. 4)
*-KQMEEEAVRLFIEWLK*NGGPSSGAPPPS-NH2              (4)

(SEQ ID NO. 5)
*-DLSK*QMEEEAVRLFIEWLKNGGPSSGAPPPS-NH2           (5)

(SEQ ID NO. 6)
*-LSK*QMEEEAVRLFIEWLKNGGPSSGAPPPS-NH2            (6)

(SEQ ID NO. 7)
*-SK*QMEEEAVRLFIEWLKNGGPSSGAPPPS-NH2             (7)

(SEQ ID NO. 8)
*-K*QMEEEAVRLFIEWLKNGGPSSGAPPPS-NH2              (8)

(SEQ ID NO. 9)
DLSK*QMEEEAVRLFIEWLK*NGGPSSGAPPPS-NH2            (9)

(SEQ ID NO. 10)
LSK*QMEEEAVRLFIEWLK*NGGPSSGAPPPS-NH2            (10)

(SEQ ID NO. 11)
SK*QMEEEAVRLFIEWLK*NGGPSSGAPPPS-NH2             (11)

(SEQ ID NO. 12)
K*QMEEEAVRLFIEWLK*NGGPSSGAPPPS-NH2              (12)
``` where, in the foregoing formulae (1) to (8), "*-" indicates that an amino group at an N-terminus is protected by a protecting group, and in the foregoing formulae (1) to (12), "K*" indicates that an amino group of a side chain of a lysine is protected by a protecting group, and "—NH₂" indicates that a carboxyl group at a C-terminus is amidated.

EFFECTS OF THE INVENTION

The molecular probe precursor for imaging of pancreatic islets according to the present invention enables imaging of pancreatic islets by, for example, positron emission tomography (PET), preferably three-dimensional imaging of pancreatic islets, and more preferably noninvasive imaging of pancreatic islets.

BRIEF DESCRIPTION OF DRAWINGS

FIGS. 1A to 1C show exemplary binding assay results from the Examples.

FIGS. 2A and 2B show exemplary resultant variations with time of biodistribution of a molecular probe of the present invention.

FIGS. 3A and 3B show exemplary results of in vivo inhibition experiments using a molecular probe of the present invention.

FIGS. 4A to 4D show exemplary results of imaging of pancreatic islets (PET) according to the present invention.

FIGS. 5A and 5B show other exemplary resultant variations with time of biodistribution of a molecular probe of the present invention.

FIGS. 6A to 6C show other exemplary results of imaging of pancreatic islets (PET) according to the present invention.

FIGS. 7A and 7B show exemplary resultant variations with time of biodistribution of a molecular probe of the present invention.

FIGS. 8A and 8B show other exemplary results of in vivo inhibition experiments using a molecular probe of the present invention.

DESCRIPTION OF THE INVENTION

Figure 1:
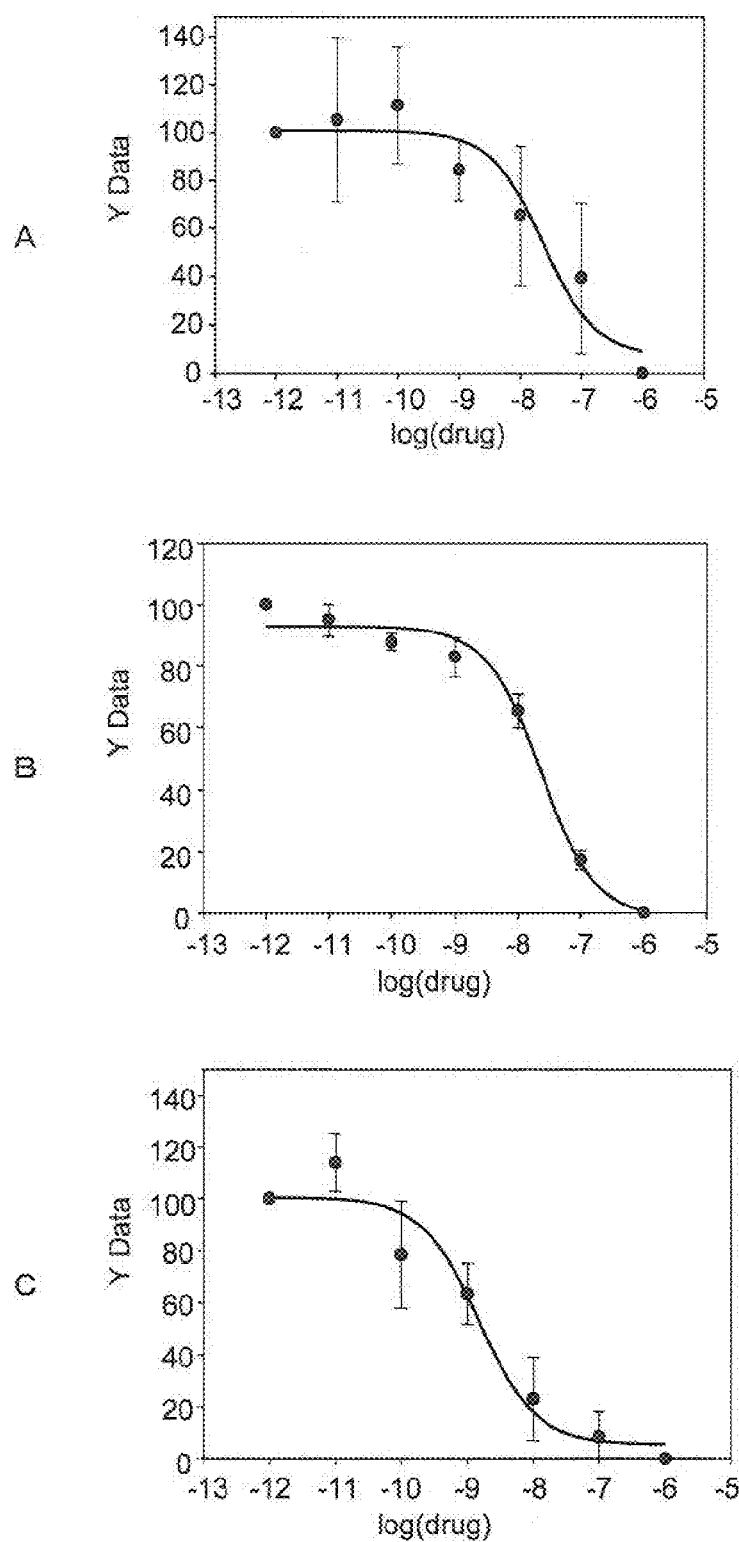
[FIG. 1]

Conventionally, $^{125}$I-labeled exendin(9-39), labeled by Bolton-Hunter labeling, has been known (e.g., NEX 335 (product code) produced by PerkinElmer Inc.). With $^{125}$I-labeled exendin(9-39), however, it has been difficult to perform noninvasive three-dimensional imaging, and it has been technically difficult to image and quantify human pancreatic islets. Though it was been known that $^{125}$I-labeled exendin (9-39) selectively and specifically accumulates in the pancreas among organs and binds selectively to pancreatic islets in the pancreas (Document 1) as described above, it has been unknown whether or not it exhibits the same behavior when it is labeled with, for example, a positron emission nuclide.

The present invention is based on the finding that when an amino group at an N-terminus of a polypeptide originating from exendin(9-39) is labeled with a positron emission nuclide, for example, noninvasive three-dimensional imaging of pancreatic islets is enabled by positron emission tomography (PET), and quantification thereof is ensured. In other words, the present invention preferably achieves an effect of enabling noninvasive three-dimensional imaging of pancreatic islets. Alternatively, the present invention preferably achieves an effect of enabling imaging of pancreatic islets for quantification. The present invention more preferably achieves an effect of enabling both of the imaging of pancreatic islets for quantification and the noninvasive three-dimensional imaging of pancreatic islets, which have been difficult conventionally.

Since the present invention enables three-dimensional imaging of pancreatic islets and the molecular probe has only one portion bound with the nuclide, the present invention preferably enables of the determination of an amount of pancreatic islets. Further, since the present invention enables noninvasive imaging, it preferably is applicable to examination and diagnosis with respect to humans. In other words, the present invention preferably enables prevention, treatment, and diagnosis of diabetes based on the determination of the amount of pancreatic islets.

Further, as described above, it is known that in the diabetes developing process, the amount of pancreatic islets decreases prior to the occurrence of glucose tolerance abnormalities. Therefore, by imaging of pancreatic islets and/or determination of the amount of pancreatic islets, for example, minute changes in the pancreatic islets can be found in a state prior to the development of diabetes or in an initial stage of the same, whereby the ultra-early detection and diagnosis of diabetes are enabled. Thus, the molecular probe precursor for imaging of pancreatic islets according to the present invention is useful for the early detection and diagnosis of diabetes, preferably for the ultra-early detection and diagnosis of diabetes.

More specifically, the present invention relates to the following:

[1] A precursor of a molecular probe for imaging of pancreatic islets, the precursor consisting of any one of the following polypeptides:

a polypeptide represented by any one of the following formulae (1) to (12);

a polypeptide obtained by deletion, insertion, or substitution of one to several amino acids with respect to a polypeptide represented by any one of the following formulae (1) to (12), the polypeptide being capable of binding to pancreatic islets after being labeled and deprotected; and a polypeptide having a homology of 80% or higher with any one of the amino acid sequences of polypeptides represented by the following formulae (1) to (12), the polypeptide being capable of binding to pancreatic islets after being labeled and deprotected, wherein the molecular probe is used in imaging of pancreatic islets,

```
                                                  (SEQ ID NO. 1)
*-DLSKQMEEEAVRLFIEWLK*NGGPSSGAPPPS-NH₂      (1)

(SEQ ID NO. 2)
 *-LSKQMEEEAVRLEIEWLK*NGGPSSGAPPPS-NH₂      (2)

(SEQ ID NO. 3)
   *-SKQMEEEAVRLFIEWLK*NGGPSSGAPPPS-NH₂     (3)

(SEQ ID NO. 4)
    *-KQMEEEAVRLFIEWLK*NGGPSSGAPPPS-NH₂     (4)

(SEQ ID NO. 5)
*-DLSK*QMEEEAVRLFIEWLKNGGPSSGAPPPS-NH₂      (5)

(SEQ ID NO. 6)
 *-LSK*QMEEEAVRLFIEWLKNGGPSSGAPPPS-NH₂      (6)

(SEQ ID NO. 7)
   *-SK*QMEEEAVRLFIEWLKNGGPSSGAPPPS-NH₂     (7)

(SEQ ID NO. 8)
    *-K*QMEEEAVRLFIEWLKNGGPSSGAPPPS-NH₂     (8)

(SEQ ID NO. 9)
DLSK*QMEEEAVRLFIEWLK*NGGPSSGAPPPS-NH₂       (9)
```

```
                                              (SEQ ID NO. 10)
LSK*QMEEEAVRLFIEWLK*NGGPSSGAPPPS-NH₂              (10)

(SEQ ID NO. 11)
SK*QMEEEAVRLFIEWLK*NGGPSSGAPPPS-NH₂               (11)

(SEQ ID NO. 12)
K*QMEEEAVRLFIEWLK*NGGPSSGAPPPS-NH₂                (12)
``` where, in the foregoing formulae (1) to (8), *- indicates that an amino group at an N-terminus is protected by a protecting group, and in the foregoing formulae (1) to (12), K* indicates that an amino group of a side chain of a lysine is protected by a protecting group, and —NH₂ indicates that a carboxyl group at a C-terminus is amidated;

[2] The precursor of the molecular probe for imaging of pancreatic islets according to [1], wherein the precursor is used in noninvasive imaging of pancreatic islets;

[3] The precursor of the molecular probe for imaging of pancreatic islets according to [1] or [2], wherein the precursor is used in imaging of pancreatic islets for quantifying an amount of pancreatic islets;

[4] The precursor of the molecular probe for imaging of pancreatic islets according to any one of [1] to [3], wherein the precursor is used in imaging of pancreatic islets for prevention, treatment, and diagnosis of diabetes;

[5] The precursor of the molecular probe for imaging of pancreatic islets according to any one of [1] to [4], wherein an amino group or lysine at an N-terminus is labeled;

[6] The precursor of the molecular probe for imaging of pancreatic islets according to any one of [1] to [5], wherein imaging of pancreatic islets is carried out by positron emission tomography (PET);

[7] A imaging of pancreatic islets method comprising labeling and deprotecting the precursor of the molecular probe for imaging of pancreatic islets according to any one of [1] to [6];

[8] The imaging of pancreatic islets method according to [7], further comprising determining a state of pancreatic islets from results of the imaging of pancreatic islets using the molecular probe;

[9] A method for determining an amount of pancreatic islets, comprising:

preparing a molecular probe for imaging of pancreatic islets, by labeling and deprotecting the precursor of a molecular probe for imaging of pancreatic islets according to any one of [1] to [6]; and determining an amount of pancreatic islets from results of imaging of pancreatic islets using the molecular probe;

[10] A method for producing a molecular probe for imaging of pancreatic islets, comprising labeling and deprotecting the precursor of the molecular probe for imaging of pancreatic islets according to any one of [1] to [6];

[11] The method according to [10], wherein the labeling of the precursor of the molecular probe for imaging of pancreatic islets is labeling of an amino group at an N-terminus or a lysine residue;

[12] A kit for preparing the molecular probe for imaging of pancreatic islets, comprising the precursor of the molecular probe for imaging of pancreatic islets according to any one of [1] to [6];

[13] A molecular probe for noninvasive imaging of pancreatic islets, being obtainable by the method according to [10] or [11];

[14] A method for diagnosis of diabetes comprising:

preparing a molecular probe for imaging of pancreatic islets by labeling and deprotecting the precursor of the molecular probe for imaging of pancreatic islets according to any one of [1] to [6];

imaging pancreatic islets by using the molecular probe for imaging of pancreatic islets; and determining a state of the pancreatic islets based on an obtained image of the pancreatic islets or a determined amount of the pancreatic islets.

[Imaging of Pancreatic Islets]

In the present invention, the "imaging of pancreatic islets" refers to "molecular imaging of pancreatic islets", and includes the imaging of in vivo spatial and/or time distribution of pancreatic islets. Further, in the present invention, the imaging of pancreatic islets preferably images pancreatic β-cells as target molecules, from the viewpoint of the prevention, treatment, and diagnosis of diabetes. Still further, in the present invention, the imaging of pancreatic islets preferably noninvasive three-dimensional imaging, from the viewpoint of the quantification of the amount of pancreatic islets, and the application of this imaging to humans. The method of imaging is not limited particularly, if it is a method that enables noninvasive imaging of pancreatic islets. Examples of the method include positron emission tomography (PET), single photon emission computed tomography (SPECT), magnetic resonance imaging (MRI), methods utilizing X-rays, visible rays, fluorescent light, near-infrared rays, ultrasonic waves, etc. Among these methods, PET is preferred, from the viewpoint of quantifying the amount of pancreatic islets using the molecular probe precursor of the present invention.

[Molecular Probe Precursor of the Present Invention]

The exemplary molecular probe precursors of the present invention include a polypeptide used in imaging of pancreatic islets, including a polypeptide represented by any one of the above-mentioned formulae (1) to (12). Amino acid sequences of polypeptides of the foregoing formulae (1) to (12) are the amino acid sequences according to SEQ ID NOS. 1 to 12 shown in the Sequence Listing, respectively. It should be noted that a protecting group is bonded to an amino group at an N-terminus of each of the polypeptides of the foregoing formulae (1) to (8), the protective group being for protecting the amino group. A carboxyl group at a C-terminus of each of the polypeptides of the foregoing formulae (1) to (12) is amidated by an amino group, from the viewpoint of improving the affinity with the pancreatic β-cell. Protecting groups are bonded to the following amino groups, in order to protecting the amino groups: amino groups of side chains of a lysine at position 19 of the polypeptide of the foregoing formula (1), of a lysine at position 18 of the polypeptide of the foregoing formula (2), of a lysine at position 17 of the polypeptide of the foregoing formula (3), and of a lysine at position 16 of the polypeptide of the foregoing formula (4); and amino groups of side chains of a lysine at position 4 of the polypeptide of the foregoing formula (5), of a lysine at position 3 of the polypeptide of the foregoing formula (6), of a lysine at position 2 of the polypeptide of the foregoing formula (7), and of a lysine at position 1 of the polypeptide of the foregoing formula (8). Therefore, if the molecular probe precursor of the present invention including the polypeptide of any of the formulae (1) to (8) is labeled with a labeling system for labeling an amino group that will be described later, an amino group of a side chain of a lysine to which no protecting group is bonded could be labeled. Further, protecting groups are bonded to the following amino groups, in order to protect the amino groups: amino groups of side chains of a lysine at position 4 and a lysine at position 19 of the polypeptide of the foregoing formula (9), of a lysine at position 3 and a lysine at position 18 of the polypeptide of the foregoing formula (10), of a lysine at position 2 and a lysine at position 17 of the polypeptide of the foregoing formula (11), and of a lysine at position 1 and a lysine at position 16 of the polypeptide of the foregoing formula (12). Therefore, if the molecular probe precursors of the present invention including the polypeptide of any of the formulae of (9) to (12) is labeled with a labeling system for labeling an amino group that will be described later, an amino group at an N-terminus of the molecular probe precursor of the present invention could be labeled.

Here, the amino acid sequences of the foregoing formula (1) (SEQ ID NO. 1 in the Sequence Listing), the foregoing formula (5) (SEQ ID NO. 5 in the Sequence Listing), and the foregoing formula (9) (SEQ ID NO. 9 in the Sequence Listing) are identical to the amino acid sequence of exendin(9-39) except that a carboxyl group at a C-terminus is amidated with an amino group and except for an amino group bonding to a protecting group. It is known that exendin(9-39) is bonding to GLP-1R (glucagon-like peptide-1 receptor) expressed on the pancreatic β-cell. The molecular probe obtained by labeling and deprotecting the Molecular probe, precursor of the present invention (this molecular probe is hereinafter referred to also as "molecular probe of the present invention") also is capable of binding to pancreatic islets, and preferably the pancreatic β-cells.

In a more preferable embodiment of the molecular probe precursor of the present invention, a protecting group for protecting an amino group preferably is bonded to an amino group of a side chain of a lysine on an N-terminus side, i.e., an amino group of a side chain of a lysine equivalent to each of the following lysine residues; a lysine residue at position 4 of SEQ ID NO. 5; a lysine residue at position 3 of SEQ ID NO. 6; a lysine residue at position 2 of SEQ ID NO. 7; and a lysine residue at position 1 of SEQ ID NO. 8. This configuration enables the imaging of pancreatic islets to be carried out more easily. Therefore, it is preferable that in the molecular probe precursor of the present invention, the lysine on the C-terminus side, i.e., a lysine equivalent to each of the following lysines, is labeled: a lysine residue at position 19 of the foregoing formula (5) (SEQ ID NO. 5); a lysine residue at position 18 of the foregoing formula (6) (SEQ ID NO. 6); a lysine residue at position 17 of the foregoing formula (7) (SEQ ID NO. 7); and a lysine residue at position 16 of the foregoing formula (8) (SEQ ID NO. 8).

In a further more preferable embodiment of the molecular probe precursor of the present invention, a protecting group for protecting an amino group more preferably is bonded to every amino group of side chains of all lysines included in a polypeptide, since this configuration enables the imaging of pancreatic islets to be carried out more easily. Therefore, in the molecular probe precursor of the present invention, the following amino groups more preferably are labeled: the amino group at the N-terminus of the foregoing formula (9) (SEQ ID NO. 9); the amino group at the N-terminus of the foregoing formula (10) (SEQ ID NO. 10); the amino group at the N-terminus of the foregoing formula (11) (SEQ ID NO. 11); and the amino group at the N-terminus of the foregoing formula (12) (SEQ ID NO. 12).

Further, other exemplary embodiments of the molecular probe precursor of the present invention includes an embodiment in which the molecular probe precursor is a polypeptide used in imaging of pancreatic islets that is obtained by deletion, insertion, or substitution of one to several amino acids with respect to any one of the polypeptides of the foregoing formulae (1) to (12), and that is capable of binding to pancreatic islets after being labeled and deprotected. Here, exemplary ranges expressed by the foregoing description of "one to several" include the following ranges: 1 to 10; 1 to 9; 1 to 8; 1 to 7; 1 to 6; 1 to 5; 1 to 4; 1 to 3; 1 to 2; and 1. In the molecular probe precursor of the present invention according to this embodiment also, in the case of a polypeptide obtained by deletion, insertion, or substitution of one to several amino acids with respect to any one of the polypeptides of the foregoing formulae (1) to (8), it is preferable that an amino group at an N-terminus is protected by a protecting group, and that a carboxyl group at a C-terminus is amidated; and in the case where one lysine to be labeled is included and another lysine also is included, an amino group of a side chain of the another lysine preferably is protected by a protecting group. Further, in the case of a polypeptide obtained by deletion, insertion, or substitution of one to several amino acids with respect to the polypeptide of any one of the foregoing formulae (9) to (12), it is preferable that a carboxyl group at a C-terminus is amidated, and that if a lysine is contained, an amino group of a side chain of the lysine is protected by a protecting group so that an amino group at an N-terminus should be labeled.

Other exemplary embodiments of the molecular probe precursor of the present invention include an embodiment in which the molecular probe precursor is a polypeptide used in imaging of pancreatic islets that has a homology of not less than 80% with the amino acid sequence of the polypeptide of any one of the foregoing formulae (1) to (12), and that is capable of binding to pancreatic islets after being labeled and deprotected. Here, the "homology" may be any value calculated by an algorithm usually used by those skilled in the art, for example BLAST or FASTA, or alternatively, it may be based on a value obtained by dividing the number of identical amino acid residues existing in two polypeptides compared, by the number of amino acids of an entire length of one of the polypeptides. Exemplary ranges of the homology may include the following ranges: not less than 85%; not less than 90%; and not less than 95%. In the molecular probe precursor of the present invention according to this embodiment also, in the case of a polypeptide having a homology of not less than 80% with the polypeptide of any one of the foregoing formulae (1) to (8), it is preferable that an amino group at an N-terminus is protected by a protecting group, and that a carboxyl group at a C-terminus is amidated; and it is preferable that one lysine to be labeled is included, and if another lysine also is included, an amino group of a side chain of the another lysine preferably is protected by a protecting group. Further, in the case of a polypeptide having a homology of not less than 80% with the polypeptide of any one of the foregoing formulae (9) to (12), it is preferable that a carboxyl group at a C-terminus is amidated, and that if a lysine other than the above-described lysines is contained, an amino group of a side chain of the lysine is protected by a protecting group so that an amino group at an N-terminus should be labeled.

The description of "being capable of binding to pancreatic islets" herein means the following: from the viewpoint of applying the present invention to the quantification of the pancreatic islets and a use of the examination and diagnosis, the molecular probe of the present invention preferably is capable of binding to the pancreatic β-cells, more preferably is at least specific to the pancreatic β-cells in the pancreas, and further more preferably is at least specific to such an extent that a signal thereof does not overlap a signal of another organ/tissue in a human body.

It should be noted that the molecular probe precursor of the present invention can be produced by peptide synthesis in accordance with a typical method, and the peptide synthesis method is not limited particularly.

The molecular probe precursor of the present invention, as described above, can be used in imaging of pancreatic islets, and preferably is used in noninvasive imaging of pancreatic islets from the viewpoint of the application of the same to the examination and diagnosis for a human, and preferably is used in imaging of pancreatic islets for quantifying the amount of the pancreatic islets from the same viewpoint. Further, the molecular probe precursor of the present invention preferably is used in imaging of pancreatic islets for the prevention and treatment for diabetes. Such imaging of pancreatic islets may be performed by positron emission tomography (PET).

[Protecting Group]

The protecting group for the molecular probe precursor of the present invention is intended to protect the other amino group than a specific amino group for the molecular probe of the present invention while the specific amino group is being labeled, the specific amino group being an amino group of a specific lysine side chain of the molecular probe precursor of the present invention, or an amino group at an N-terminus of the molecular probe precursor of the present invention. As the protecting group, any known protecting group capable of performing such a function can be used. The protecting group is not limited particularly, and examples of the same include 9-fluorenylmethyloxycarbonyl group (Fmoc), tert-butoxycarbonyl group (Boc), benzyloxycarbonyl group (Cbz), 2,2,2-trichloroethoxycarbonyl group (Troc), and allyloxycarbonyl group (Alloc). From the viewpoint of handleability, Fmoc and Boc are preferable. Deprotecting methods with respect to these protecting groups are known, respectively, and those skilled in the art are able to performing deprotection appropriately.

The molecular probe precursor of the present invention may have a configuration in which, for example, fluorobenzoyl (FB) or iodobenzoyl (IB) may be bonded to a specific amino group to be labeled, that is, an amino group of a specific lysine side chain of the molecular probe precursor of the present invention or an amino group at an N-terminus of the molecular probe precursor of the present invention. Alternatively, the molecular probe precursor of the present invention may have a configuration in which, for example, a chelate site bondable to a metal radioactive isotope (metal nuclide) or a linker site. Examples of the metal nuclide include $^{62}$Cu, $^{64}$Cu, $^{67}$Ga, $^{68}$Ga, $^{82}$Rb, $^{99m}$Tc, and $^{111}$In. Examples of the chelate compound include diethylenetriaminepentaacetic acid (DTPA), 6-hydrazinoeulysin-3-carboxylic acid (HYNIC), tetraazacyclododecanetetraacetic acid (DOTA), dithisosemicarbazone (DTS), diaminedithiol (DADT), mercaptoacetylglycylglycylglycine (MAG3), monoamidemonoaminedithiol (MAMA), diamidedithiol (DADS), and propylene diamine dioxime (PnAO).

[Method of Preparation of Molecular Probe of the Present Invention]

The molecular probe of the present invention can be prepared by labeling the molecular probe precursor of the present invention according to an imaging method, and thereafter, deprotecting the same by removing a protecting group. Exemplary nuclides used in labeling include positron emission nuclides such as $^{11}$C, $^{13}$N, $^{15}$O, $^{18}$F, $^{62}$Cu, $^{64}$Cu, $^{68}$Ga, and $^{82}$Rb; and single photon emission nuclides such as $^{67}$Ga, $^{99m}$Tc, $^{111}$In, and $^{123}$I. Exemplary labeling procedures are as follows: when PET is performed as an imaging method, a positron emission nuclide such as $^{11}$C, $^{15}$O, or $^{18}$F is labeled by a known method; and when SPECT is performed as an imaging method, a single photon emission such as $^{99m}$Tc, $^{111}$In, or $^{123}$I is labeled by a known method. The known labeling method is, for example, SFB (N-succinimidyl 4-fluorobenzoate) or SIB (N-succinimidyl 3-iodobenzoate). When the labeling is carried out using a metal nuclide, the labeling is performed using, for example, the above-described chelate compound. When the polypeptides (1) to (8) shown above are labeled by these methods, the following amino groups are labeled: the amino groups of side chains of a lysine at position 4 of the polypeptide of the foregoing formula (1), of a lysine at position 3 of the polypeptide of the foregoing formula (2), of a lysine at position 2 of the polypeptide of the foregoing formula (3), and of a lysine at position 1 of the polypeptide of the foregoing formula (4); and the amino groups of side chains of a lysine at position 19 of the polypeptide of the foregoing formula (5), of a lysine at position 18 of the polypeptide of the foregoing formula (6), of a lysine at position 17 of the polypeptide of the foregoing formula (7), and of a lysine at position 16 of the polypeptide of the foregoing formula (8). Besides, when the polypeptides of the foregoing formulae (9) to (12) are labeled by the foregoing method, the amino groups at N-termini of the polypeptides of the foregoing formulae (9) to (12) are labeled. However, the labeling methods in the present invention are not limited to these methods. The deprotecting after the labeling can be carried out by a known method in accordance with the type of the protecting group. Therefore, another aspect of the present invention relates to a method for producing the molecular probe of the present invention, the method including labeling and deprotecting the molecular probe precursor of the present invention. Further, in the method for producing the molecular probe of the present invention, the labeling of the molecular probe precursor of the present invention preferably is the labeling of an amino group at an N-terminus.

Still another aspect of the present invention relates to a molecular probe for noninvasive imaging of pancreatic islets obtained by the method for producing the molecular probe of the present invention. With the molecular probe for imaging of pancreatic islets according to the present invention, the noninvasive three-dimensional imaging of pancreatic islets can be performed. The molecular probe of the present invention may have a configuration in which the following nuclide is bonded thereto: metal nuclides such as $^{62}$Cu, $^{64}$Cu, $^{67}$Ga, 82Rb, $^{99m}$Tc, and $^{111}$In; and nuclides such as $^{11}$C, $^{13}$N, $^{15}$O, $^{18}$F, and $^{123}$I. Further, the molecular probe of the present invention may have a configuration in which, for example, the aforementioned chelate compound to which the foregoing metal nuclide is bonded, or a linker site serving in linkage between a specific amino group of the peptide and a chelate site having a metal nuclide bonded thereto.

[Imaging Method]

Still another aspect of the present invention relates to a method for imaging pancreatic islets including labeling the molecular probe precursor according to the present invention and thereafter deprotecting the precursor by removing a protecting group. The method for imaging pancreatic islets according to the present invention may include imaging pancreatic islets using the molecular probe of the present invention. The method for imaging pancreatic islets according to the present invention preferably is a method for imaging pancreatic β-cells, from the viewpoint of applying the present invention to the examination and diagnosis. The labeling and deprotection of the precursor is as described above, and the imaging of pancreatic islets also is as described above. The method for imaging pancreatic islets according to the present invention may further include determining a state of pancreatic islets based on a result of the imaging of pancreatic islets using the above-described molecular probe. The determining of a state of pancreatic islets based on a result of the imaging of pancreatic islets using the molecular probe includes, for example, determining presence/absence of pancreatic islets by analyzing an image of the imaging of pancreatic islets, and determining an increase/decrease in an amount of pancreatic islets.

The method for imaging pancreatic islets according to the present invention may include administering the molecular probe thus prepared of the present invention to a subject, and performing the determination by means of positron emission tomography (PET) or another means after a lapse of a predetermined time period since the administration of a molecular probe. The determination by PET or the like includes, for example, picking up an image, and determining an amount of pancreatic islets. Examples of the subject include humans and mammals other than humans. The administration to a subject may be local administration or systemic administration. A path for administration may be determined appropriately according to a state of a subject and the like, and it may be, for example, intravenous, intraarterial, intradermal, and intraabdominal injection or infusion. The molecular probe of the present invention preferably is administered together with a carrier. Examples usable as the carrier include aqueous solvents and non-aqueous solvents. Examples of the aqueous solvent include potassium phosphate buffer solution, physiologic saline, Ringer's solution, and distilled water Examples of the non-aqueous solvent include polyethylene glycol, vegetable fats and oils, ethanol, glycerol, dimethyl sulfoxide, and propylene glycol. The amount of the molecular probe of the present invention for imaging of pancreatic islets or determining an amount of pancreatic islets may be set to be, for example, not more than 1 µg. The time period from the administration to the determination may be decided appropriately according to, for example, a time necessary for the molecular probe to be bound to pancreatic islets, the type of the molecular probe, the decomposition time of the molecular probe, etc.

[Method for Determining Amount of Pancreatic Islets]

Still another aspect of the present invention relates to a method for determining an amount of pancreatic islets, including preparing the molecular probe of the present invention by labeling and deprotecting the molecular probe precursor of the present invention, and determining an amount of pancreatic islets from a result of imaging of pancreatic islets using the molecular probe. The method for determining an amount of pancreatic islets according to the present invention may include imaging of pancreatic islets using the molecular probe thus prepared of the present invention. The labeling and the deprotecting are as described above, and the imaging of pancreatic islets also is as described above. The calculation of an amount of pancreatic islets from a result of imaging of pancreatic islets using the molecular probe may be performed by, for example, analyzing an image obtained by imaging of pancreatic islets. The quantification of a subject of the imaging from a result of the imaging can be performed easily by any person skilled in the art, using a calibration curve, an appropriately program, or the like. The method for determining an amount of pancreatic islets according to the present invention preferably is a method for determining an amount of pancreatic β cells from the viewpoint of applying the same to the examination and diagnosis.

[Methods for Prevention, Treatment, and Diagnosis of Diabetes]

Still another aspect of the present invention relates to a method for prevention, treatment, or diagnosis of diabetes. Specifically, the method for prevention, treatment, or diagnosis of diabetes of the present invention includes preparing a molecular probe for imaging of pancreatic islets by labeling and deprotecting a molecular probe precursor for imaging of pancreatic islets according to the present invention; imaging the pancreatic islets using the molecular probe for imaging of pancreatic islets; and determining a state of the pancreatic islets based on an obtained image of the pancreatic islets or a determined amount of the pancreatic islets, thereby diagnosing diabetes. The method may further include performing prevention or treatment for diabetes based on the foregoing diagnosis. As described above, in the diabetes developing process, the amount of pancreatic islets (particularly, the amount of pancreatic β-cells) decreases prior to the occurrence of glucose tolerance abnormalities, and therefore, when functional abnormalities are detected or there are subjective symptoms, diabetes has already reached the stage where it is too difficult to be treated. With the imaging method using the molecular probe precursor of the present invention and/or the method for determining an amount of the pancreatic islets using the molecular probe precursor of the present invention, however, a decrease in the amount of the pancreatic islets and/or the amount of the pancreatic β-cells can be detected at an early stage, and further, new methods for prevention, treatment, and diagnosis of diabetes can be created. As to a subject on which prevention, treatment, and diagnosis of diabetes is carried out, examples of the subject include humans and mammals other than humans. For example, the method for prevention of diabetes may include regularly determining an amount of pancreatic islets, and checking presence/absence of a tendency of a decrease in the amount of pancreatic islets. Further, the method of treatment for diabetes of the present invention may include evaluating an effect of treatment such as medication and diet performed on a subject, focusing on a change in an amount of pancreatic islets. Still further, the method for diagnosis of diabetes of the present invention may include imaging pancreatic islets or determining an amount of pancreatic islets, and comparing the result with a reference size or amount of the pancreatic islets, or determining development of diabetes.

Still another preferable aspect of the present invention relates to an ultra-early diagnosis of diabetes. The ultra-early diagnosis method for diabetes of the present invention may include, for example, imaging pancreatic islets or determining an amount of pancreatic islets in, for example, comprehensive or ordinary medical examination by the method of the present invention; and determining a state of the pancreatic islets based on the obtained image of the pancreatic islets or the determined amount of the pancreatic islets. Further, a method of treatment for diabetes of the present invention may include imaging pancreatic islets or determining an amount of pancreatic islets by the method of the present invention; and evaluating functional recovery of the pancreatic islets based on the obtained image of the pancreatic islets or the determined amount of the pancreatic islets.

[Kit]

Still another aspect of the present invention also relates to a kit including the molecular probe precursor of the present invention. Examples of embodiments of the kit of the present invention include a kit for preparing the molecular probe of the present invention, a kit for performing the imaging method of the present invention, a kit for performing the method for determining an amount of pancreatic islets according to the present invention, and a kit for prevention, treatment, or diagnosis of diabetes according to the present invention. Preferably, in each of these embodiments, the kit includes an instruction manual suitable for the embodiment.

The kit of the present invention may further include, for example, a component used for preparing a molecular probe such as a buffer or an osmotic regulator, and an instrument used in administration of a molecular probe, such as a syringe.

Hereinafter, the present invention will be described further by way of examples. It should be noted that the present invention is, when interpreted, not limited to the following examples.

EXAMPLES

[Binding Assay]

First, the following three types of molecular probe precursors were prepared: a molecular probe precursor of the above-described formula (1), which has a configuration in which a protecting group was bonded to a lysine residue at position 19 in SEQ ID NO. 1; a molecular probe precursor of the above-described formula (5), which has a configuration in which a protecting group was bonded to a lysine residue at position 4 in SEQ ID NO. 5; and a molecular probe precursor of the above-described formula (9), which has a configuration in which protecting groups were bonded to a lysine residue at position 4 and a lysine residue at position 19 in SEQ ID NO. 9. It should be noted that as the protecting group, Fmoc was used. Further, a carboxyl group at a C-terminus of each molecular probe precursor was amidated.

Next, the above-described molecular probe precursor (200 μg) was dissolved in borate buffer (pH 7.8), and [$^{19}$F]SFB was added thereto so that the reaction solution had a pH of 8.5 to 9.0. Thus, the precursor was labeled. Thereafter, DMF and piperidine were added thereto so as to cause a deprotecting reaction, whereby the three types of intended molecular probes X, Y, and Z were obtained. More specifically, the molecular probe X was a molecular probe obtained using the molecular probe precursor of the above-described formula (1), and had a configuration in which a [$^{19}$F] fluorobenzoyl group was bonded to a side chain in a lysine at position 4 and a carboxyl group at a C-terminus was amidated in the amino acid sequence of SEQ ID NO. 1. The molecular probe Y was a molecular probe obtained using the molecular probe precursor of the above-described formula (5), and had a configuration in which a [$^{19}$F] fluorobenzoyl group was bonded to a lysine residue at position 19 and a carboxyl group at a C-terminus was amidated in the amino acid sequence of SEQ ID NO. 5. The molecular probe Z was a molecular probe obtained using the molecular probe precursor of the above-described formula (9), and had a configuration in which a [$^{19}$F] fluorobenzoyl group was bonded to an amino group at an N-terminus and a carboxyl group at a C-terminus was amidated in the amino acid sequence of SEQ ID NO. 9.

Next, pancreatic islets isolated from a mouse were dispersed over single cells, so that $1.7 \times 10^5$ pancreatic islets were present per sample. A solution containing $^{125}$I labeled exendin(9-39) labeled by Bolton-Hunter labeling was added to the cells thus prepared so that a final concentration of the $^{125}$I labeled exendin(9-39) was 0.1 μCi (0.045 pmol; 0.153 ng/100 μl). Subsequently, reagents containing the prepared molecular probes X, Y, and Z, respectively, were added to the cells to which the $^{125}$I labeled exendin(9-39) had been added (final concentration of each molecular probe: $1 \times 10^{-6}$ to $1 \times 10^{-12}$ M), and was incubated at room temperature for one hour. The reaction was stopped by filtration, and a radioactivity was determined using a liquid scintillation analyzer. The results of the determination are shown in FIGS. 1A to 1C.

FIGS. 1A to 1C were graphs showing exemplary results of an analysis with SigmaPlot11 (trade name). FIG. 1A shows exemplary results as to the molecular probe X. FIG. 1B shows exemplary results as to the molecular probe Y. FIG. 1C shows exemplary results as to the molecular probe Z. As shown in FIGS. 1A to 1C, all of the molecular probes X, Y, and Z exhibited concentration-dependent inhibition against the binding of GLP-1R and $^{125}$I labeled exendin(9-39). Further, IC$_{50}$ of the molecular probe X was $2.35 \times 10^{-8}$ M, IC$_{50}$ of the molecular probe Y was $2.36 \times 10^{-8}$ M, and IC$_{50}$ of the molecular probe Z was $1.5 \times 10^{-9}$ M.

Example 1

Using the molecular probe precursor of the above-described formula (1) of the present invention, which has a configuration in which protecting groups were bonded to an N-terminus and a lysine residue at position 19 of SEQ ID NO. 1 in the Sequence Listing, biodistribution of the same in a mouse was determined, and three-dimensional imaging of pancreatic islets of the mouse was carried out. First, a molecular probe of the present invention was prepared in the following manner.

[Preparation of Molecular Probes]

The molecular probe precursor (500 μg) of the above-described formula (1) in which Fmoc was used as a protecting group was dissolved in borate buffer (pH 7.8). [$^{18}$F]SFB was added thereto so that pH of the reaction solution was adjusted to 8.5 to 9.0. Thus, the precursor was labeled. Thereafter, DMF and piperidine were added thereto so as to cause a deprotecting reaction, whereby the intended product (molecular probe having a configuration in which a lysine residue at position 4 was labeled in SEQ ID NO. 1) was obtained. In other words, the obtained molecular probe had a configuration in which [$^{18}$F]FB (fluorobenzoyl group) bound to an amino group of a side chain of a lysine at position 4 and a carboxyl group at a C-terminus therein was amidated in the amino acid sequence of SEQ ID NO. 1.

[Biodistribution]

Figure 2:
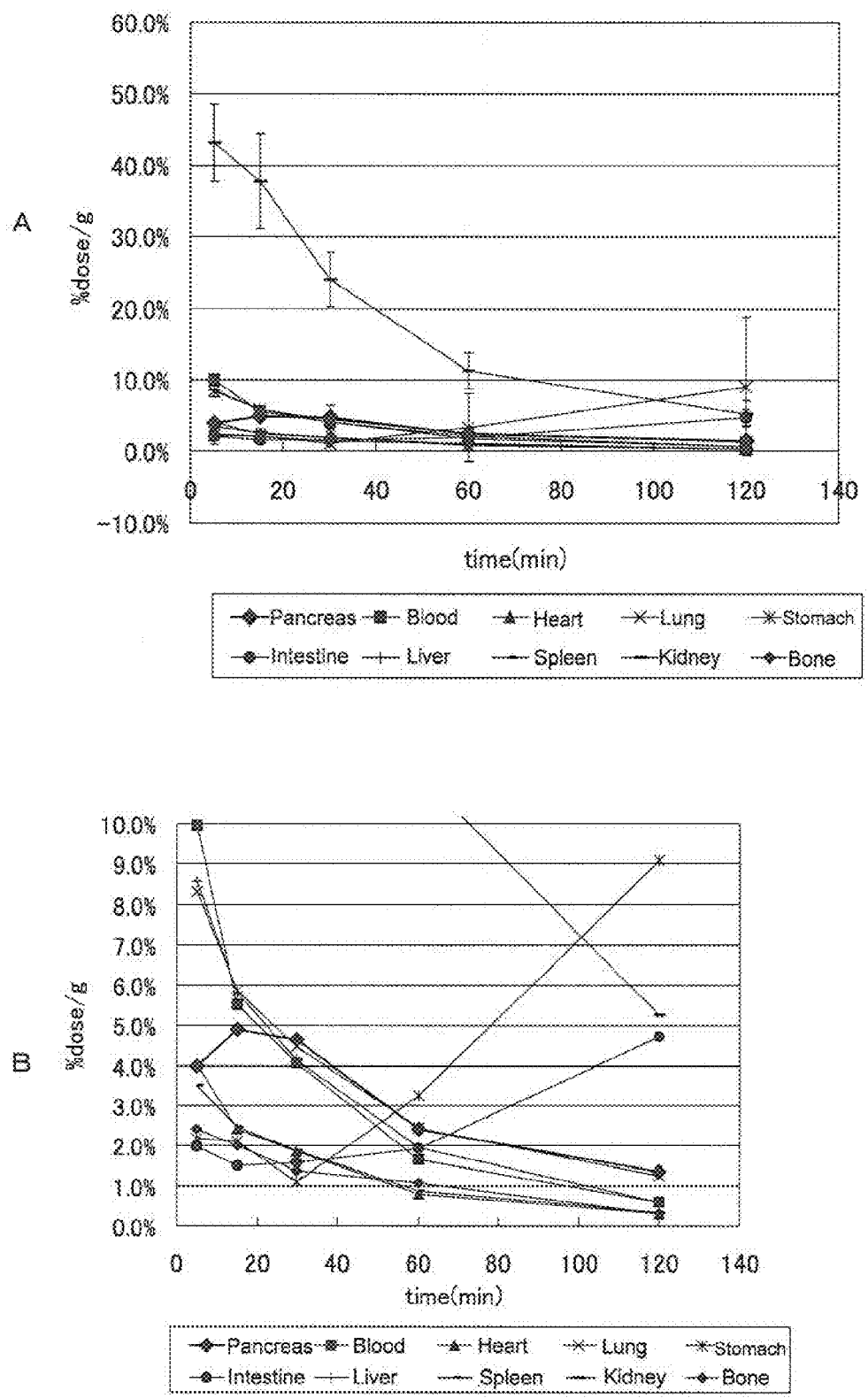
[FIG. 2]

The probe thus prepared (69 μCi) was administered to unanesthetized 6-week-old ddY mice (male, weight: 30 g) by intravenous injection (through the tail vein). When 5 minutes, 15 minutes, 30 minutes, 60 minutes, and 120 minutes had passed since the administration, organs were dissected out of the mice, respectively (n=5). The weight and the radioactivity of each organ were determined, and an accumulation amount (% dose/g) of the probe was calculated from the radioactivity per unit weight. Exemplary results are shown in FIGS. 2A and 2B. FIG. 2A is a graph showing how the accumulation of the molecular probe in each organ varied with time, and FIG. 2B is a graph zooming in on FIG. 2A As shown in FIGS. 2A and 2B, the accumulation of the molecular probe prepared in the present example into the pancreas was 4% dose/g when 5 minutes had passed since the administration, 4.9% dose/g when 15 minutes had passed since the administration, and 4.7% dose/g when 30 minutes had passed since the administration. During a time period from the point of 5 minutes to the point of 40 minutes after the administration, the molecular probe prepared in the present example accumulated more in the pancreas than in the stomach or the intestines as the organs adjacent to the pancreas. This suggests that the molecular probe allows a PET image with a contrast enough for observation to be obtained.

[In Vivo Inhibition Experiments]

With the molecular probe prepared as described above (the molecular probe having a configuration in which an amino group of a side chain of a lysine at position 4 was labeled and a carboxyl group at a C-terminus therein was amidated in the amino acid sequence of SEQ ID NO. 1 in the Sequence Listing), in vivo inhibition experiments were carried out. 6-week-old ddY mice (male, weight: 30 g) were used.

First, non-labeled exendin (9-39) (cold probe) (0.1 mL of 0.5 mg/mL solution) was administered by intravenous injection to unanesthetized mice preliminarily. When 30 minutes had passed since the foregoing preliminary administration, the prepared molecular probe (52 µCi) was administered by intravenous injection to the mice. When 30 minutes had passed since the administration of the molecular probe, each organs were dissected out (n=5). The weight and the radioactivity of each organ were determined, and an accumulation amount (% dose/g) of the probe was calculated from the radioactivity per unit weight. Exemplary results are shown in FIGS. 3A and 3B.

The prepared molecular probe (52 µCi) was administered by intravenous injection to unanesthetized mice, without a cold probe being administered thereto preliminarily, and these mice were used as controls. When 30 minutes had passed since the administration, each organ was dissected out (n=5). The weight and the radioactivity of each organ were determined, and an accumulation amount (% dose/g) of the probe was calculated from the radioactivity per unit weight. Exemplary results are shown in FIGS. 3A and 3B, together with the results obtained in the case where the preliminary administration was carried out (hereinafter such a case is referred to as "preliminary administration cases").

Figure 3:
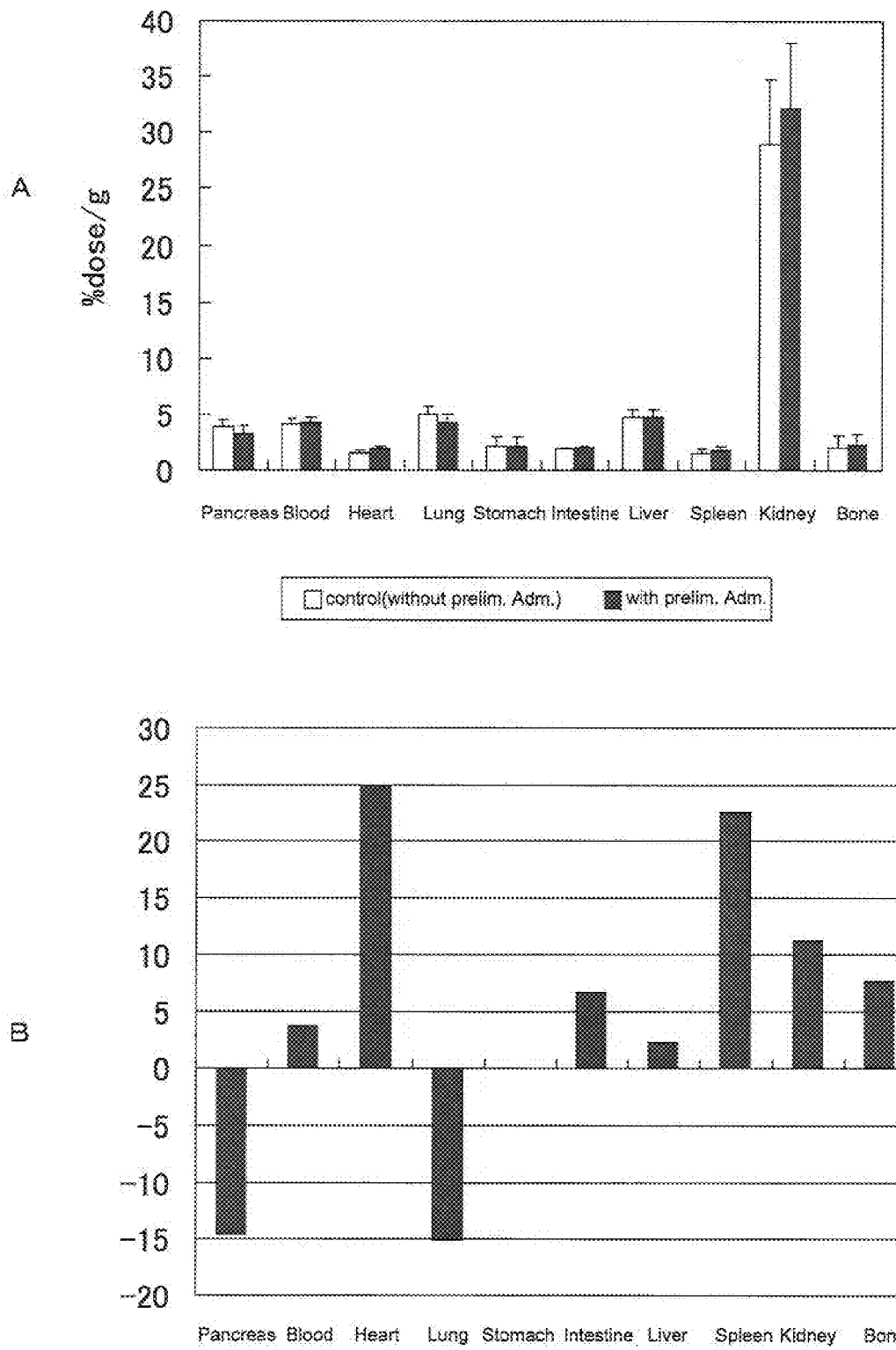
[FIG. 3]

FIG. 3A is a graph showing accumulation amounts (% dose/g) of the probe in the preliminary administration case and accumulation amounts (% dose/g) of the probe in the case of the controls (hereinafter referred to as a control case), and FIG. 3B is a graph showing a ratio of inhibition caused by the preliminary administration of the cold probe (={(accumulation amount in the preliminary administration case)−(accumulation amount in the control case)}/(accumulation amount in the control case)×100). As shown in FIGS. 3A and 3B, it is observed that with the preliminary administration of a cold probe, which inhibited the binding of the molecular probe to a receptor, the accumulation amount of the prepared molecular probe by the pancreas was inhibited by about 15%.

[Three-Dimensional Imaging]

The prepared molecular probe (82 µCi) was administered by intravenous injection to anesthetized 6-week-old ddY mice (male, weight: 30 g), and were subjected to three-dimensional imaging with the following PET device and under the following conditions:

Imaging device: eXplore Vista (trade name, manufactured by GE)

Scan mode: Static scan

Reconstruction: 2DOSEM (Dynamic OS-EM)

Figure 4:
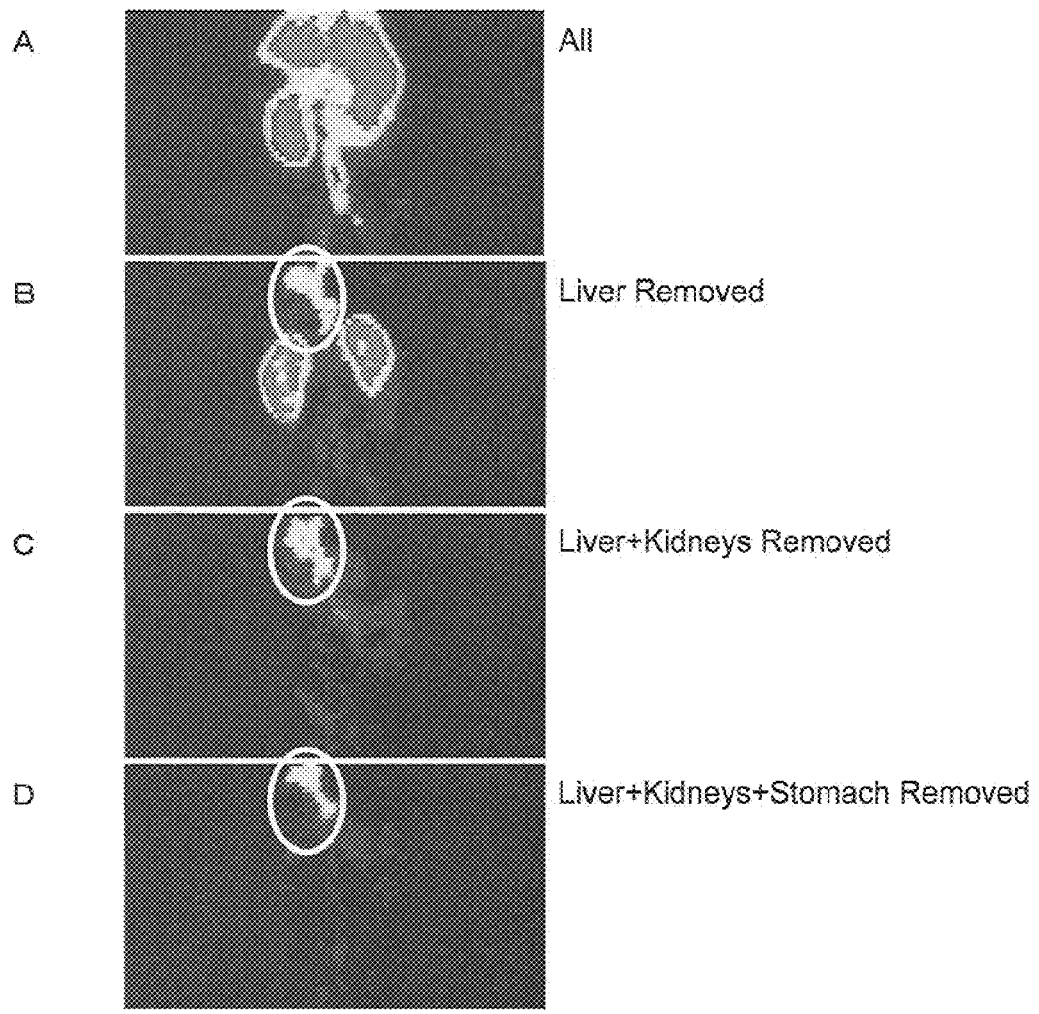
[FIG. 4]

Exemplary results of the three-dimensional imaging are shown in FIGS. 4A to 4D. The images are those obtained when 8 minutes had passed since the administration of the molecular probe. FIGS. 4A to 4D are coronal views of the three-dimensional imaging: FIG. 4A (integrating time: 15 minutes) shows an image of an entire mouse (without any excision); FIG. 4B (integrating time: 10 minutes) shows an image of the mouse after the liver was excised; FIG. 4C (integrating time: 10 minutes) shows an image of the mouse after the kidneys, in addition to the liver, were excised; and FIG. 4D (integrating time: 15 minutes) shows an image of the mouse after the liver, the kidneys, and the stomach were excised. All of the images in FIGS. 4A to 4D are about the same mouse. In each of FIGS. 4B to 4D, a white circle indicates the position of the pancreas. In the images of FIGS. 4A to 4D, the degrees of contrast are at the same level.

As shown in FIGS. 4A to 4D, the three-dimensional imaging of the pancreas was enabled by the molecular probe precursor of the present invention. It should be noted that in the case of a mouse, as shown in FIG. 4A, the position of the pancreas was difficult to determine, since the liver and the pancreas are very close to each other and the resolution of PET used was 1.4 mm, which is different from the case of a human whose organs have large sizes and are located separately. Therefore, it is suggested that with the molecular probe precursor of the present invention, noninvasive three-dimensional imaging of pancreatic islets could be carried out with respect to a human Example 2

Using the molecular probe precursor of the above-described formula (5) of the present invention, which has a configuration in which protecting groups were bonded to amino groups at an N-terminus and a lysine residue at position 4 in SEQ ID NO. 5, biodistribution of the same in a mouse was determined, and three-dimensional imaging of pancreatic islets of the mouse was carried out. First, a molecular probe of the present invention was prepared in the following manner.

[Preparation of Molecular Probes]

The molecular probe precursor (500 µg) of the above-described formula (5), in which Fmoc was used as a protecting group, was dissolved in borate buffer (pH 7.8). [$^{18}$F]SFB was added thereto so that pH of the reaction solution was adjusted to 8.5 to 9.0. Thus, the precursor was labeled. Thereafter, DMF and piperidine were added thereto so as to cause a deprotecting reaction, whereby the intended product (molecular probe having a configuration in which a lysine residue at position 19 was labeled in SEQ ID NO. 5) was obtained. In other words, the obtained molecular probe had a configuration in which [$^{18}$F]FB bound to an amino group of a side chain of a lysine at position 19 and a carboxyl group at a C-terminus therein was amidated in the amino acid sequence of SEQ ID NO. 5.

[Biodistribution]

Figure 5:
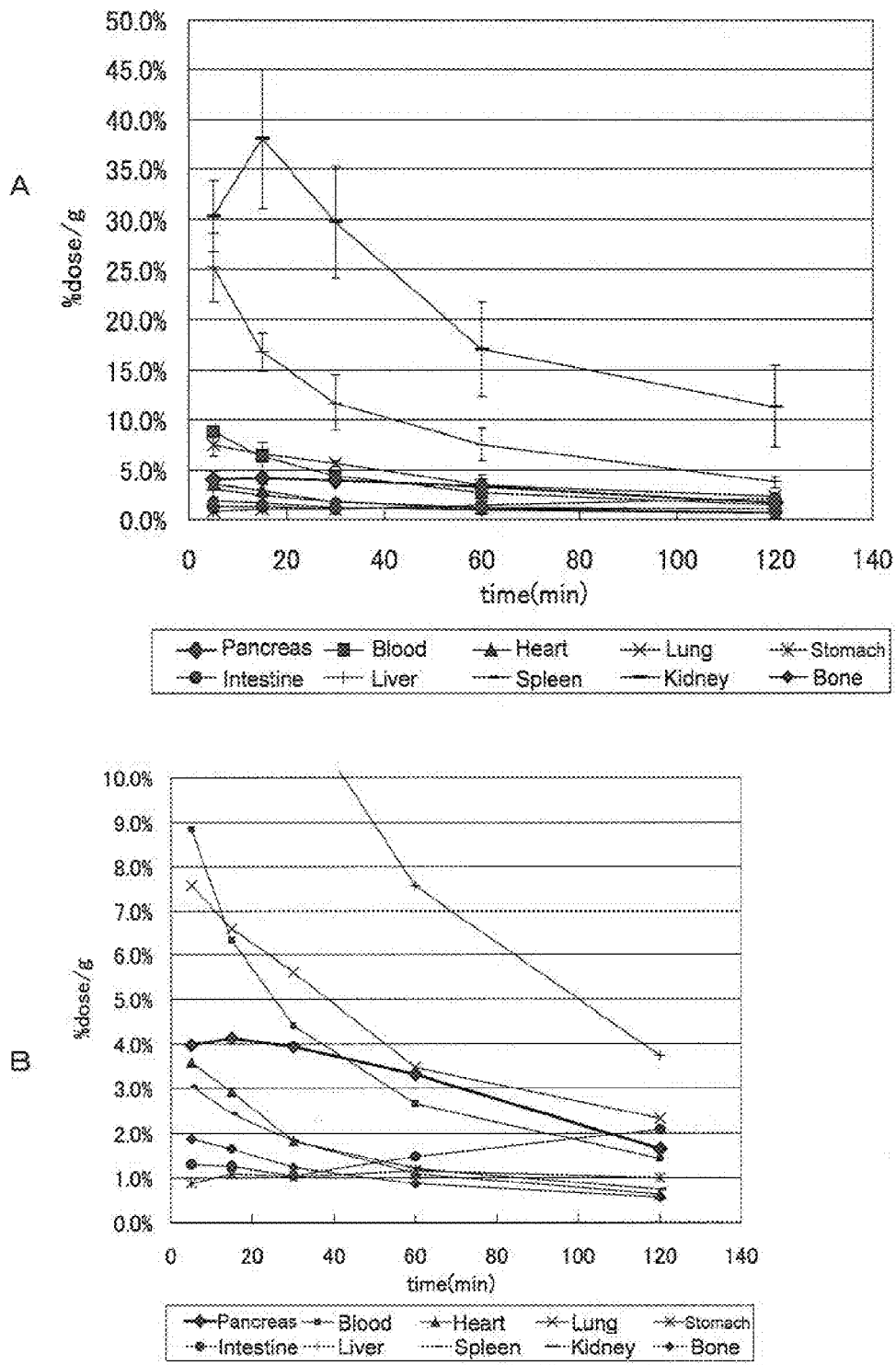
[FIG. 5]

The molecular probe thus prepared (67 µCi) was administered to unanesthetized 6-week-old ddY mice (male, weight: 30 g) by intravenous injection (through the tail vein). When 5 minutes, 15 minutes, 30 minutes, 60 minutes, and 120 minutes had passed since the administration, organs were dissected out of the mice, respectively (n=5). The weight and the radioactivity of each organ were determined, and an accumulation amount (% dose/g) of the probe was calculated from the radioactivity per unit weight. Exemplary results are shown in FIGS. 5A and 5B. FIG. 5A is a graph showing how the accumulation of the molecular probe in each organ varied with time, and FIG. 5B is a graph zooming in on FIG. 5B.

As shown in FIGS. 5A and 5B, the accumulation of the molecular probe prepared in the present example into the pancreas was 4% dose/g when 5 minutes had passed since the administration, 4.1% dose/g when 15 minutes had passed since the administration, and 3.9% dose/g when 30 minutes had passed since the administration. Regarding the biodistribution, as compared with the molecular probe prepared in Example 1 (molecular probe having a configuration in which a lysine residue at position 4 was labeled in SEQ ID NO. 1), the molecular probe prepared in the present example (molecular probe having a configuration in which a lysine residue at position 19 was labeled in SEQ ID NO. 5) exhibited smaller accumulation in the stomach and the intestines as organs adjacent to the pancreas, though exhibiting greater accumulation in the liver. Besides, the variation with time of the accumulation of the molecular probe in the stomach and the intestine is significantly smaller. These suggest a possibility that the use of the molecular probe having a configuration in which a lysine residue at position 19 is labeled in SEQ ID NO.

5, or the use of the molecular probe having a configuration in which a lysine corresponding to the lysine on the C-terminus side is labeled, makes it possible to obtain a PET image with a further higher contrast, when the pancreatic islets are observed.

[Three-Dimensional Imaging]

Figure 6:
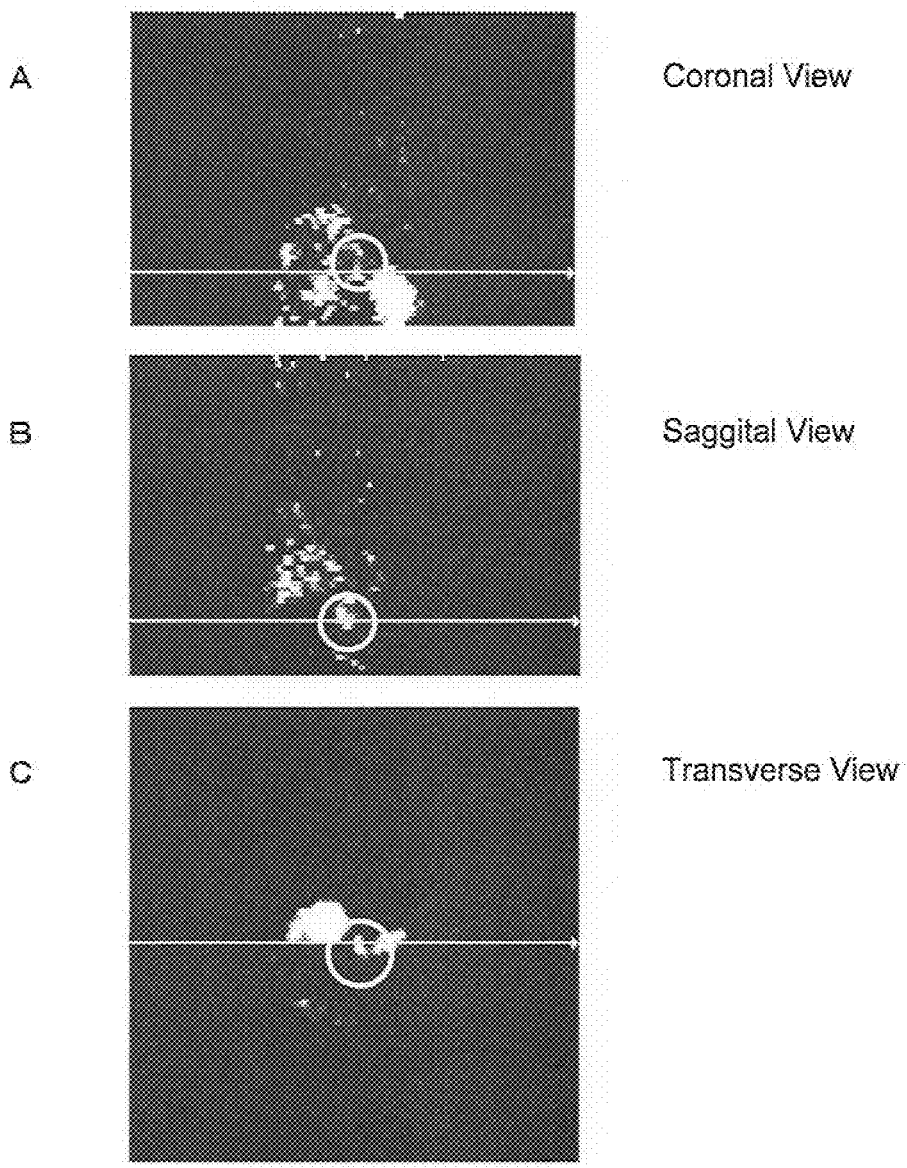
[FIG. 6]

The prepared molecular probe (174 µCi) prepared in the present example was administered by intravenous injection to anesthetized 7-week-old ddY mice (male, weight: 32 g), and were subjected to three-dimensional imaging under the same conditions as those in Example 1. Exemplary results obtained are shown in FIGS. 6A to 6C. The images are those obtained when 30 minutes had passed since the administration of the molecular probe (integrating time: 10 minutes). FIG. 6A is a coronal view of the three-dimensional imaging, FIG. 6B is a sagittal view of the three-dimensional imaging, and FIG. 6C is a transverse view of the three-dimensional imaging. In each of FIGS. 6A to 6C, a white circle indicates the position of the pancreas, and organs that are seen white on both sides to the pancreas (white circle) in FIG. 6C (traverse view) are the kidneys. In the images of FIGS. 6A to 6C, the degrees of contrast are at the same level.

As shown in FIGS. 6A to 6C, noninvasive, clear determination of the position of the pancreas was enabled using the molecular probe precursor of the present invention of the above-described formula (5). In other words, noninvasive three-dimensional imaging of pancreatic islets was enabled by the molecular probe precursor of the present invention.

Example 3

Using the molecular probe precursor of the above-described formula (9) of the present invention, which is formed of a polypeptide of SEQ ID NO. 9, in which protecting groups were bonded to a lysine residue at position 4 and a lysine residue at position 19 and a carboxyl group at a C-terminus thereof was amidated, a molecular probe of the present invention was prepared in the following manner.

[Preparation of Molecular Probe]

The molecular probe precursor (500 µg) of the above-described formula (9) in which Fmoc was used as a protecting group was dissolved in borate buffer (pH 7.8). [$^{18}$F]SFB was added thereto so that pH of the reaction solution was adjusted to 8.5 to 9.0. Thus, the precursor was labeled. Thereafter, DMF and piperidine were added thereto so as to cause a deprotecting reaction, whereby the intended product (molecular probe having a configuration in which an amino group at an N-terminus was labeled in the amino acid sequence of SEQ ID NO. 9 in the Sequence Listing) was obtained. In other words, the obtained molecular probe had a configuration in which [$^{18}$F]FB bound to an amino group at an N-terminus and a carboxyl group at a C-terminus therein was amidated in the amino acid sequence of SEQ ID NO. 9.

Using the molecular probe prepared as described above, biodistribution of the same in a mouse was determined, and in vivo inhibition experiments were carried out.

[Biodistribution]

Figure 7:
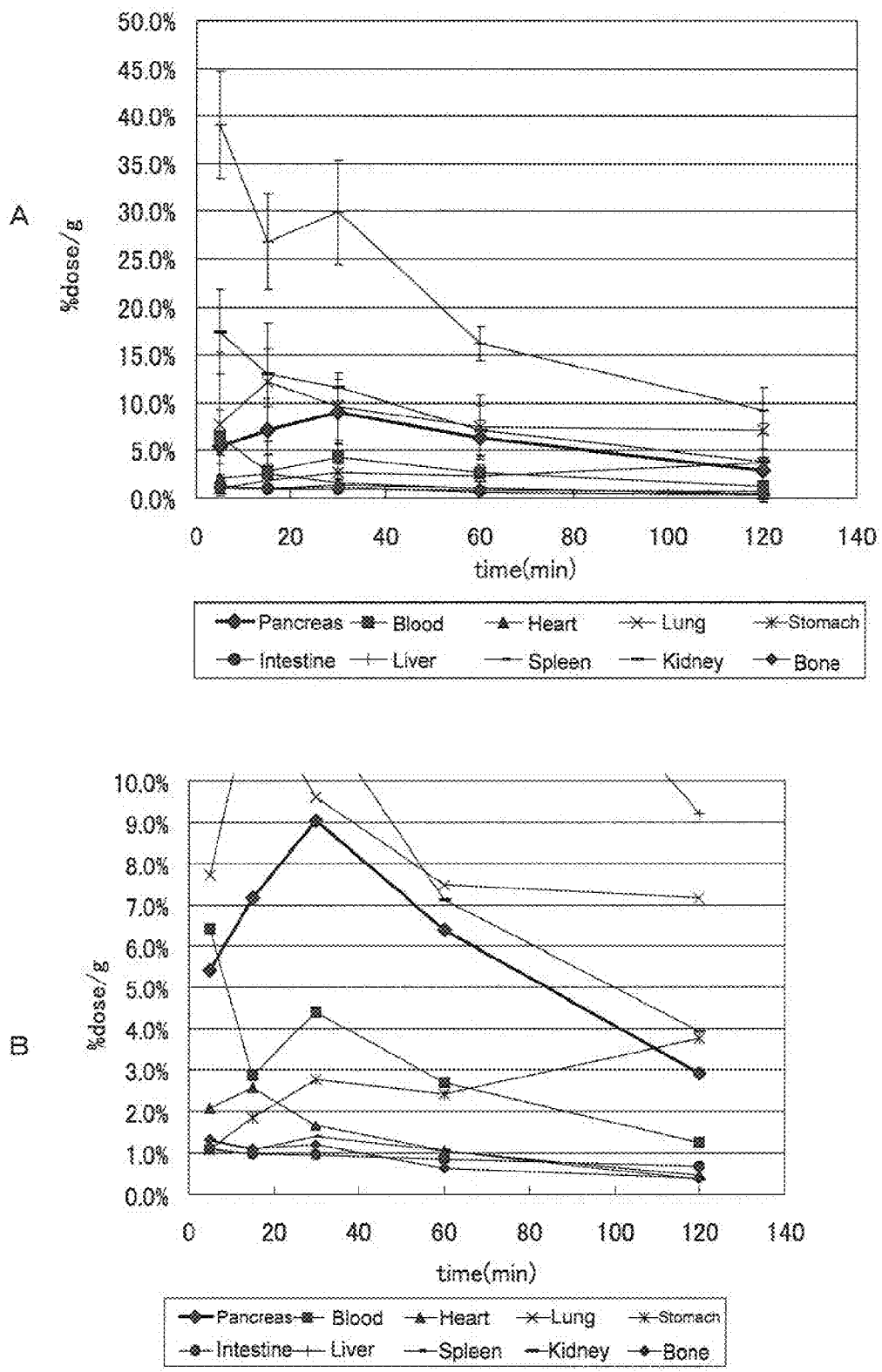
[FIG. 7]

The molecular probe thus prepared (13 µCi) was administered to unanesthetized 6-week-old ddY mice (male, weight: 30 g) through the tail vein. When 5 minutes, 15 minutes, 30 minutes, 60 minutes, and 120 minutes had passed since the administration, organs were dissected out of the mice, respectively (n=5). The weight and the radioactivity of each organ were determined, and an accumulation amount (% dose/g) of the probe was calculated from the radioactivity per unit weight. Exemplary results are shown in FIGS. 7A and 7B. FIG. 7A is a graph showing how the accumulation of the molecular probe in each organ varied with time, and FIG. 7B is a graph zooming in on FIG. 7A.

As shown in FIGS. 7A and 7B, the accumulation of the molecular probe prepared in the present example into the pancreas was 5.4% dose/g when 5 minutes had passed since the administration, 7.2% dose/g when 15 minutes had passed since the administration, 9.0% dose/g when 30 minutes had passed since the administration, and 6.4% dose/g when 60 minutes had passed since the administration. Besides, in the case of the molecular probe prepared in the present example, the accumulation of the probe at a level exceeding 5% dose/g in the pancreas was maintained for a long time, and particularly during a period from 15 minutes to 50 minutes since the administration, the accumulation of the probe in the pancreas exceeded 7% dose/g. Further, as compared with the molecular probe of Example 1 (FIGS. 2A and 2B) and the molecular probe of Example 2 (FIGS. 5A and 5B), the molecular probe prepared in Example 3 exhibited the greatest accumulation in the pancreas. These suggested a possibility that a molecular probe in which an amino group at an N-terminus is labeled is suitable for picking up a PET image, and the use of this molecular probe makes it possible to obtain a high-contrast PET image when the pancreas is observed.

[In Vivo Inhibition Experiments]

With the molecular probe prepared as described above (the molecular probe having a configuration in which an amino group at an N-terminus and a carboxyl group at a C-terminus in the same was amidated in the amino acid sequence of SEQ ID NO. 9 in the Sequence Listing), in vivo inhibition experiments were carried out. 6-week-old ddY mice (male, weight: 30 g) were used.

First, non-labeled exendin (9-39) (0.1 mL of 0.5 mg/mL solution) was administered by intravenous injection to unanesthetized mice preliminarily. When 30 minutes had passed since the foregoing preliminary administration, the prepared molecular probe (17 µCi) was administered by intravenous injection to the mice. When 30 minutes had passed since the administration of the molecular probe, each organs were dissected out (n=5). The weight and the radioactivity of each organ were determined, and an accumulation amount (% dose/g) of the probe was calculated from the radioactivity per unit weight. Exemplary results are shown in FIGS. 8A and 8B.

The prepared molecular probe (17 µCi) was administered by intravenous injection to unanesthetized mice, without a cold probe being administered thereto preliminarily, and these mice were used as controls. When 30 minutes had passed since the administration, each organ was dissected out (n=5). The weight and the radioactivity of each organ were determined, and an accumulation amount (% dose/g) of the probe was calculated from the radioactivity per unit weight. Exemplary results are shown in FIGS. 8A and 8B, together with the results obtained in the preliminary administration case.

Figure 8:
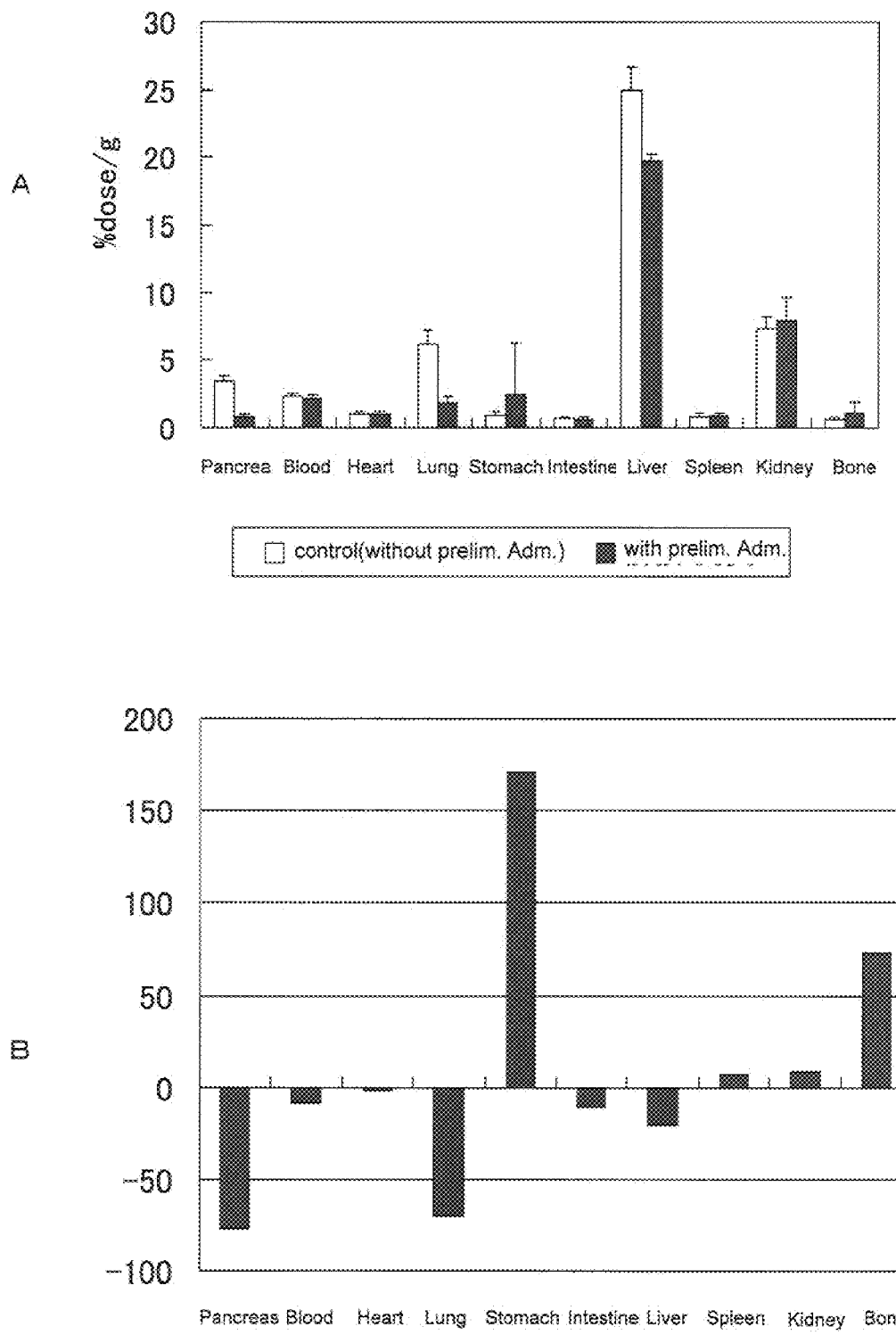
[FIG. 8]

FIG. 8A is a graph showing accumulation amounts (% dose/g) of the probe in the preliminary administration case and accumulation amounts (% dose/g) of the probe in the control case, and FIG. 8B is a graph showing a ratio of inhibition caused by the preliminary administration of the cold probe (={(accumulation amount in the preliminary administration case)−(accumulation amount in the control case)}/(accumulation amount in the control case)×100). As shown in FIGS. 8A and 8B, it is observed that with the preliminary administration of a cold probe, which inhibited the binding of the molecular probe to a receptor, the accumulation amount of the prepared molecular probe by the pancreas was inhibited by 75% or more. Thus, it W was confirmed that the molecular probe having a configuration in which an amino group at an N-terminus was labeled and a carboxyl group at a C-terminus was amidated in the amino acid sequence of SEQ ID NO. 9 in the Sequence Listing was specifically taken into pancreatic n-cells in mice.

The foregoing results suggested that the molecular probe precursor of the present invention enables noninvasive three-dimensional imaging of the pancreas, and particularly, noninvasive three-dimensional imaging of pancreatic n-cells, in humans.

Industrial Applicability

As described above, the present invention is useful in, for example, the medical field, the molecule imaging field, and the field relating to diabetes.

Sequence Listing Free Text

SEQ ID NOS. 1 to 12: the amino acid sequences of the molecular probe precursors of the present invention.

The invention claimed is:

1. A precursor polypeptide comprising any one of the following polypeptides:
   a polypeptide represented by any one of the following formulae (1) to (12);
   a polypeptide obtained by deletion, insertion, or substitution of one, two or three amino acids with respect to a polypeptide represented by any one of the following formulae (1) to (12), the polypeptide binding to pancreatic islets after being labeled and deprotected; and
   a polypeptide having a sequence identity of 85% or higher with any one of the amino acid sequences of polypeptides represented by the following formulae (1) to (12), the polypeptide binding to pancreatic islets after being labeled and deprotected,
   wherein the molecular probe is used in pancreatic islet imaging,

```
*-DLSKQMEEEAVRLFIEWLK*NGGPSSGAPPPS-NH₂     (SEQ ID NO. 1)
                                              (1)

*-LSKQMEEEAVRLFIEWLK*NGGPSSGAPPPS-NH₂      (SEQ ID NO. 2)
                                              (2)

*-SKQMEEEAVRLFIEWLK*NGGPSSGAPPPS-NH₂       (SEQ ID NO. 3)
                                              (3)

*-KQMEEEAVRLFIEWLK*NGGPSSGAPPPS-NH₂        (SEQ ID NO. 4)
                                              (4)

*-DLSK*QMEEEAVRLFIEWLKNGGPSSGAPPPS-NH₂     (SEQ ID NO. 5)
                                              (5)

*-LSK*QMEEEAVRLFIEWLKNGGPSSGAPPPS-NH₂      (SEQ ID NO. 6)
                                              (6)
```

-continued

```
                                                 (SEQ ID NO. 7)
*-SK*QMEEEAVRLFIEWLENGGPSSGAPPPS-NH₂                  (7)

(SEQ ID NO. 8)
*-K*QMEEEAVRLFIEWLKNGGPSSGAPPPS-NH₂                   (8)

(SEQ ID NO. 9)
DLSK*QMEEEAVRLFIEWLK*NGGPSSGAPPPS-NH₂                 (9)

(SEQ ID NO. 10)
LSK*QMEEEAVRLFIEWLK*NGGPSSGAPPPS-NH₂                  (10)

(SEQ ID NO. 11)
SK*QMEEEAVRLFIEWLK*NGGPSSGAPPPS-NH₂                   (11)

(SEQ ID NO. 12)
K*QMEEEAVRLFIEWLK*NGGPSSGAPPPS-NH₂                    (12)
``` wherein, in the foregoing formulae (1) to (8), "*-" indicates that an amino group at an N-Terminus is protected by a protecting group, and in the foregoing formulae (1) to (12), "K*" indicates that an amino group of a side chain of a lysine is protected by a protecting group, the functional groups of the side chains of the amino acids except for K* are not protected by a protecting group, and "—NH₂" indicates that a carboxyl group at a C-terminus is amidated.

2. The precursor polypeptide according to claim 1, wherein the precursor polypeptide comprises the polypeptide represented by any one of the formulae (1) to (12).

3. The precursor polypeptide according to claim 1, wherein the precursor polypeptide consists of the polypeptide represented by any one of the formulae (1) to (12).

4. The precursor polypeptide according to claim 1, wherein the precursor polypeptide comprises a polypeptide obtained by deletion, insertion or substitution of one amino acid of any of the polypeptides represented by the formulae (1) to (12).

5. The precursor polypeptide according to claim 1, wherein the precursor polypeptide comprises a polypeptide obtained by deletion, insertion or substitution of two amino acids of any of the polypeptides represented by formulae (1) to (12).

6. The precursor polypeptide according to claim 1, wherein the precursor polypeptide comprises a polypeptide having a sequence identity of 95% or higher with any one of the amino acid sequences of polypeptides represented by the formulae (1) to (12).

7. A pancreatic islet imaging method comprising labeling and deprotecting the precursor polypeptide according to claim 1.

8. The pancreatic islet imaging method according to claim 7, wherein the precursor is used in noninvasive pancreatic islet imaging.

9. The pancreatic islet imaging method according to claim 7, wherein the precursor is used in pancreatic islet imaging for quantitating an amount of pancreatic islets.

10. The pancreatic islet imaging method according to claim 7, wherein the precursor is used in pancreatic islet imaging for prevention, treatment, and diagnosis of diabetes.

11. The pancreatic islet imaging method according to claim 7, wherein an amino group or lysine at an N-terminus is labeled.

12. The pancreatic islet imaging method according to claim 7, wherein pancreatic islet imaging is carried out by positron emission tomography (PET).

13. The pancreatic islet imaging method according to claim 7, further comprising determining a state of pancreatic islets from results of the pancreatic islet imaging using the deprotected polypeptide.

14. A method of determining an amount of pancreatic islets, comprising:
preparing a molecular probe for pancreatic islet imaging by labeling and deprotecting the precursor polypeptide according to claim 1; and
determining the amount of pancreatic islets from results of pancreatic islet imaging using the molecular probe.

15. A method of producing a molecular probe for pancreatic islet imaging, comprising labeling and deprotecting the precursor polypeptide according to claim 1.

16. The method according to claim 15, wherein the labeling of the precursor polypeptide is labeling of an amino group at an N-terminus or a lysine residue.

17. A kit for preparing the molecular probe for pancreatic islet imaging, comprising the precursor polypeptide according to claim 1.

18. A molecular probe produced by the method according to claim 15 or 16.

19. A method of diagnosing diabetes comprising:
preparing a molecular probe for pancreatic islet imaging by labeling and deprotecting the precursor polypeptide according to claim 1;
imaging pancreatic islets by contacting the molecular probe with pancreatic islets; and
determining a state of the pancreatic islets based on an obtained image of the pancreatic islets or a determined amount of the pancreatic islets bound to the molecular probe.

* * * * *